United States Patent
Bernotas et al.

(10) Patent No.: US 7,238,696 B2
(45) Date of Patent: Jul. 3, 2007

(54) HETEROCYCLYL-3-SULFONYLINDAZOLES AS 5-HYDROXYTRYPTAMINE-6 LIGANDS

(75) Inventors: Ronald Charles Bernotas, Royersford, PA (US); Yinfa Yan, Bedminster, NJ (US); Albert Jean Robichaud, Ringoes, NJ (US); Guangcheng Liu, Princeton Junction, NJ (US)

(73) Assignee: Wyeth, Madison, NJ (US)

( * ) Notice: Subject to any disclaimer, the term of this patent is extended or adjusted under 35 U.S.C. 154(b) by 350 days.

(21) Appl. No.: 10/778,427

(22) Filed: Feb. 13, 2004

(65) Prior Publication Data

US 2004/0167122 A1   Aug. 26, 2004

Related U.S. Application Data

(60) Provisional application No. 60/447,613, filed on Feb. 14, 2003.

(51) Int. Cl.
*A61K 31/496* (2006.01)
*C07D 403/04* (2006.01)
*C07D 409/14* (2006.01)

(52) U.S. Cl. .................. 514/254.06; 544/371; 540/575; 540/603; 546/199; 546/275.7; 514/218; 514/322

(58) Field of Classification Search ................ 544/371; 514/254.06
See application file for complete search history.

(56) References Cited

U.S. PATENT DOCUMENTS

| 6,391,872 B1 | 5/2002 | Marfat |
| 6,509,357 B1 | 1/2003 | Zhou et al. |
| 6,613,781 B2 | 9/2003 | Zhou et al. |
| 6,727,246 B2 | 4/2004 | Bernotas et al. |
| 6,767,912 B2 | 7/2004 | Zhou et al. |
| 6,831,094 B2 | 12/2004 | Li et al. |
| 2002/0115670 A1 | 8/2002 | Kelly et al. |
| 2003/0069278 A1 | 4/2003 | Zhou et al. |
| 2004/0023970 A1 | 2/2004 | Bernotas et al. |
| 2004/0024023 A1 | 2/2004 | Bernotas et al. |
| 2004/0024210 A1 | 2/2004 | Johansson et al. |
| 2004/0138286 A1 | 7/2004 | Imazaki et al. |
| 2004/0167030 A1 | 8/2004 | Bernotas et al. |
| 2005/0113283 A1 | 5/2005 | Solow-Cordero et al. |

FOREIGN PATENT DOCUMENTS

| WO | WO 97/49699 A1 | 12/1997 |
| WO | WO 03/013510 A1 | 2/2003 |
| WO | WO 03/080580 A2 | 10/2003 |
| WO | WO 03/080608 A2 | 10/2003 |

*Primary Examiner*—Emily Bernhardt
(74) *Attorney, Agent, or Firm*—Barbara L. Lences

(57) ABSTRACT

The present invention provides a compound of formula I and the use thereof in the therapeutic treatment of disorders related to or affected by the 5-HT6 receptor

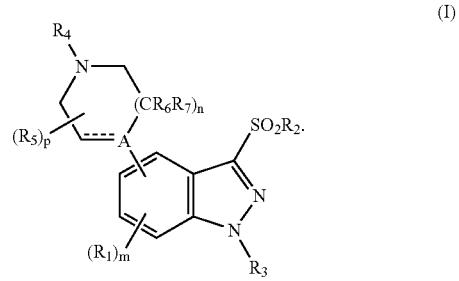

14 Claims, No Drawings

HETEROCYCLYL-3-SULFONYLINDAZOLES AS 5-HYDROXYTRYPTAMINE-6 LIGANDS

This application claims priority from copending provisional application No. 60/447,613 filed on Feb. 14, 2003, the entire disclosure of which is hereby incorporated by reference.

BACKGROUND OF THE INVENTION

Serotonin (5-Hydroxytryptamine)(5-HT) receptors play a critical role in many physiological and behavioral functions in humans and animals. These functions are mediated through various 5-HT receptors distributed throughout the body. There are now approximately fifteen different human 5-HT receptor subtypes that have been cloned, many with well-defined roles in humans. One of the most recently identified 5-HT receptor subtypes is the 5-HT6 receptor, first cloned from rat tissue in 1993 (Monsma, F. J.; Shen, Y.; Ward, R. P.; Hamblin, M. W. *Molecular Pharmacology* 1993, 43, 320–327) and subsequently from human tissue (Kohen, R.; Metcalf, M. A.; Khan, N.; Druck, T.; Huebner, K.; Sibley, D. R. *Journal of Neurochemistry* 1996, 66, 47–56). The receptor is a G-protein coupled receptor (GPCR) positively coupled to adenylate cyclase (Ruat, M.; Traiffort, E.; Arrang, J-M.; Tardivel-Lacombe, L.; Diaz, L.; Leurs, R.; Schwartz, J-C. *Biochemical Biophysical Research Communications* 1993, 193, 268–276). The receptor is found almost exclusively in the central nervous system (CNS) areas both in rat and in human. In situ hybridization studies of the 5-HT6 receptor in rat brain using mRNA indicate principal localization in the areas of 5-HT projection including striatum, nucleus accumbens, olfactory tubercle, and hippocampal formation (Ward, R. P.; Hamblin, M. W.; Lachowicz, J. E.; Hoffman, B. J.; Sibley, D. R.; Dorsa, D. M. *Neuroscience* 1995, 64, 1105–1111).

There are many potential therapeutic uses for 5-HT6 ligands in humans based on direct effects and on indications from available scientific studies. These studies include the localization of the receptor, the affinity of ligands with known in vivo activity, and various animal studies conducted so far.

One potential therapeutic use of modulators of 5-HT6 receptor function is in the enhancement of cognition and memory in human diseases such as Alzheimer's. The high levels of receptor found in important structures in the forebrain, including the caudate/putamen, hippocampus, nucleus accumbens, and cortex suggest a role for the receptor in memory and cognition since these areas are known to play a vital role in memory (Gerard, C.; Martres, M.-P.; Lefevre, K.; Miquel, M. C.; Verge, D.; Lanfumey, R.; Doucet, E.; Hamon, M.; El Mestikawy, S. *Brain Research*, 1997, 746, 207–219). The ability of known 5-HT6 receptor ligands to enhance cholinergic transmission also supported the potential cognition use (Bentley, J. C.; Boursson, A.; Boess, F. G.; Kone, F. C.; Marsden, C. A.; Petit, N.; Sleight, A. J. *British Journal of Pharmacology*, 1999, 126(7), 1537–1542). Studies have found that a known 5-HT6 selective antagonist significantly increased glutamate and aspartate levels in the frontal cortex without elevating levels of noradrenaline, dopamine, or 5-HT. This selective elevation of neurochemicals known to be involved in memory and cognition strongly suggests a role for 5-HT6 ligands in cognition (Dawson, L. A.; Nguyen, H. Q.; Li, P. *British Journal of Pharmacology*, 2000, 130(1), 23–26). Animal studies of memory and learning with a known selective 5-HT6 antagonist found some positive effects (Rogers, D. C.; Hatcher, P. D.; Hagan, J. J. *Society of Neuroscience, Abstracts* 2000, 26, 680). Further support for the role of a selective 5-HT6 ligand in cognition can be found in Woolley, M. L.; Marsden, C. A.; Sleight, A. J.; and Fone, K. C. F., *Psychopharmacology*, 2003, 170(4), 358–367.

A related potential therapeutic use for 5-HT6 ligands is the treatment of attention deficit disorders (ADD, also known as Attention Deficit Hyperactivity Disorder or ADHD) in both children and adults. Because 5-HT6 antagonists appear to enhance the activity of the nigrostriatal dopamine pathway and because ADHD has been linked to abnormalities in the caudate (Ernst, M; Zametkin, A. J.; Matochik, J. H.; Jons, P. A.; Cohen, R. M. *Journal of Neuroscience* 1998, 18(15), 5901–5907), 5-HT6 antagonists may attenuate attention deficit disorders.

Early studies examining the affinity of various CNS ligands with known therapeutic utility or a strong structural resemblance to known drugs suggests a role for 5-HT6 ligands in the treatment of schizophrenia and depression. For example, clozapine (an effective clinical antipsychotic) has high affinity for the 5-HT6 receptor subtype. Also, several clinical antidepressants have high affinity for the receptor as well and act as antagonists at this site (Branchek, T. A.; Blackburn, T. P. *Annual Reviews in Pharmacology and Toxicology* 2000, 40, 319–334).

Further, recent in vivo studies in rats indicate 5-HT6 modulators may be useful in the treatment of movement disorders including epilepsy (Stean, T.; Routledge, C.; Upton, N. *British Journal of Pharmacology* 1999, 127 Proc. Supplement 131P and Routledge, C.; Bromidge, S. M.; Moss, S. F.; Price, G. W.; Hirst, W.; Newman, H.; Riley, G.; Gager, T.; Stean, T.; Upton, N.; Clarke, S. E.; Brown, A. M. *British Journal of Pharmacology* 2000, 130(7), 1606–1612).

Taken together, the above studies strongly suggest that compounds which are 5-HT6 receptor modulators, i.e. ligands, may be useful for therapeutic indications including: the treatment of diseases associated with a deficit in memory, cognition, and learning such as Alzheimer's and attention deficit disorder; the treatment of personality disorders such as schizophrenia; the treatment of behavioral disorders, e.g., anxiety, depression and obsessive compulsive disorders; the treatment of motion or motor disorders such as Parkinson's disease and epilepsy; the treatment of diseases associated with neurodegeneration such as stroke and head trauma; or withdrawal from drug addiction including addiction to nicotine, alcohol, and other substances of abuse.

Therefore, it is an object of this invention to provide compounds which are useful as therapeutic agents in the treatment of a variety of central nervous system disorders related to or affected by the 5-HT6 receptor.

It is another object of this invention to provide therapeutic methods and pharmaceutical compositions useful for the treatment of central nervous system disorders related to or affected by the 5-HT6 receptor.

It is a feature of this invention that the compounds provided may also be used to further study and elucidate the 5-HT6 receptor.

SUMMARY OF THE INVENTION

The present invention provides a compound of formula I

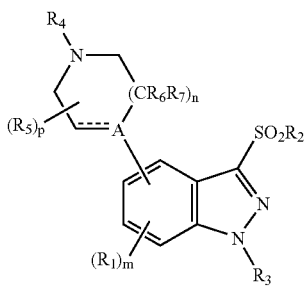

wherein

A is C, $CR_8$ or N;

$R_1$ is H, halogen, CN, $COR_9$, $OCO_2R_{10}$, $CO_2R_{11}$, $CONR_{12}R_{13}$, $SO_xR_{14}$, $NR_{15}R_{16}$, $OR_{17}$ or a $C_1$–$C_6$alkyl, $C_3$–$C_7$cycloalkyl, aryl or heteroaryl group each optionally substituted;

$R_2$ is an optionally substituted $C_1$–$C_6$alkyl, $C_3$–$C_7$cycloalkyl, aryl, or heteroaryl group or an optionally substituted 8- to 13-membered bicyclic or tricyclic ring system having a N atom at the bridgehead and optionally containing 1, 2 or 3 additional heteroatoms selected from N, O or S;

$R_3$ is H or a $C_1$–$C_6$alkyl, $C_3$–$C_7$cycloalkyl, aryl or heteroaryl group each optionally substituted;

$R_4$ is H or a $C_1$–$C_6$alkyl or $C_3$–$C_7$cycloalkyl group each optionally substituted;

$R_5$, $R_6$ and $R_7$ are each independently H or a $C_1$–$C_6$alkyl or $C_3$–$C_7$cycloalkyl group each optionally substituted;

m and p are each independently an integer of 1, 2 or 3;

n is an integer of 1 or 2;

$R_8$ is H, OH or an optionally substituted $C_1$–$C_6$alkoxy group;

$R_9$, $R_{10}$, $R_{11}$, and $R_{17}$ are each independently H or a $C_1$–$C_6$alkyl, $C_2$–$C_6$alkenyl, $C_2$–$C_6$alkynyl, $C_3$–$C_6$cycloalkyl, cycloheteroalkyl, aryl or heteroaryl group each optionally substituted;

$R_{12}$, $R_{13}$, $R_{15}$ and $R_{16}$ are each independently H or an optionally substituted $C_1$–$C_4$alkyl group or $R_{12}$ and $R_{13}$ or $R_{15}$ and $R_{16}$ may be taken together with the atom to which they are attached to form a 5- to 7-membered ring optionally containing another heteroatom selected from O, $NR_{18}$ or $SO_x$;

$R_{14}$ is a $C_1$–$C_6$alkyl, $C_2$–$C_6$alkenyl, $C_2$–$C_6$alkynyl, $C_3$–$C_6$cycloalkyl, cycloheteroalkyl, aryl or heteroaryl group each optionally substituted;

$R_{18}$ is H or a $C_1$–$C_6$alkyl, $C_2$–$C_6$alkenyl, $C_2$–$C_6$alkynyl, $C_3$–$C_7$cycloalkyl, cycloheteroalkyl, aryl or heteraryl group each optionally substituted;

x is 0 or an integer of 1 or 2; and

----- represents a single bond or a double bond; or the stereoisomers thereof or the pharmaceutically acceptable salts thereof.

The present invention also provides methods and compositions useful in the treatment of central nervous system disorders.

DETAILED DESCRIPTION OF THE INVENTION

The 5-hydroxytryptamine-6 (5-HT6) receptor is one of the most recent receptors to be identified by molecular cloning. Its ability to bind a wide range of therapeutic compounds used in psychiatry, coupled with its intriguing distribution in the brain has stimulated significant interest in new compounds which are capable of interacting with or affecting said receptor. Significant efforts are being made to understand the possible role of the 5-HT6 receptor in psychiatry, cognitive dysfunction, motor function and control, memory, mood and the like. To that end, compounds which demonstrate a binding affinity for the 5-HT6 receptor are earnestly sought both as an aid in the study of the 5-HT6 receptor and as potential therapeutic agents in the treatment of central nervous system disorders, for example see C. Reavill and D. C. Rogers, Current Opinion in Investigational Drugs, 2001, 2(1):104–109, Pharma Press Ltd.

Surprisingly, it has now been found that heterocyclyl-3-sulfonylindazoles of formula I demonstrate 5-HT6 affinity along with significant sub-type selectivity. Advantageously, said formula I indazoles are effective therapeutic agents for the treatment of central nervous system (CNS) disorders associated with or affected by the 5-HT6 receptor. Accordingly, the present invention provides 1-heterocyclyl-3-sulfonylindazole compounds of formula I

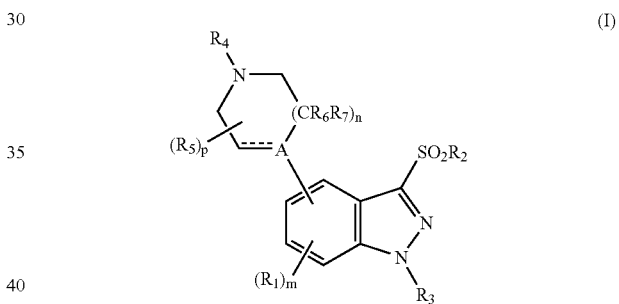

wherein

A is C, $CR_8$ or N;

$R_1$ is H, halogen, CN, $COR_9$, $OCO_2R_{10}$, $CO_2R_{11}$, $CONR_{12}R_{13}$, $SO_xR_{14}$, $NR_{15}R_{16}$, $OR_{17}$ or a $C_1$–$C_6$alkyl, $C_3$–$C_7$cycloalkyl, aryl or heteroaryl group each optionally substituted;

$R_2$ is an optionally substituted $C_1$–$C_6$alkyl, $C_3$–$C_7$cycloalkyl, aryl, or heteroaryl group or an optionally substituted 8- to 13-membered bicyclic or tricyclic ring system having a N atom at the bridgehead and optionally containing 1, 2 or 3 additional heteroatoms selected from N, O or S;

$R_3$ is H or a $C_1$–$C_6$alkyl, $C_3$–$C_7$cycloalkyl, aryl or heteroaryl group each optionally substituted;

$R_4$ is H or a $C_1$–$C_6$alkyl or $C_3$–$C_7$cycloalkyl group each optionally substituted;

$R_5$, $R_6$ and $R_7$ are each independently H or a $C_1$–$C_6$alkyl or $C_3$–$C_7$cycloalkyl group each optionally substituted;

m and p are each independently an integer of 1, 2 or 3;

n is an integer of 1 or 2;

$R_8$ is H, OH or an optionally substituted $C_1$–$C_6$alkoxy group;

$R_9$, $R_{10}$, $R_{11}$ and $R_{17}$ are each independently H or a $C_1$–$C_6$alkyl, $C_2$–$C_6$alkenyl, $C_2$–$C_6$alkynyl, $C_3$–$C_6$cycloalkyl, cycloheteroalkyl, aryl or heteroaryl group each optionally substituted;

$R_{12}$, $R_{13}$, $R_{15}$ and $R_{16}$ are each independently H or an optionally substituted $C_1$–$C_4$alkyl group or $R_{12}$ and $R_{13}$ or $R_{15}$ and $R_{16}$ may be taken together with the atom to which they are attached to form a 5- to 7-membered ring optionally containing another heteroatom selected from O, $NR_{18}$ or $SO_x$;

$R_{14}$ is a $C_1$–$C_6$alkyl, $C_2$–$C_6$alkenyl, $C_2$–$C_6$alkynyl, $C_3$–$C_6$cycloalkyl, cycloheteroalkyl, aryl or heteroaryl group each optionally substituted;

$R_{18}$ is H or a $C_1$–$C_6$alkyl, $C_2$–$C_6$alkenyl, $C_2$–$C_6$alkynyl, $C_3$–$C_7$cycloalkyl, cycloheteroalkyl, aryl or heteraryl group each optionally substituted;

x is 0 or an integer of 1 or 2; and

----represents a single bond or a double bond; or the stereoisomes thereof or the pharmaceutically acceptable salts thereof.

As used in the specification and claims, the term halogen designates F, Cl, Br or I and the term cycloheteroalkyl designates a five- to seven-membered cycloalkyl ring system containing 1 or 2 heteroatoms, which may be the same or different, selected from N, O or S and optionally containing one double bond. Exemplary of the cycloheteroalkyl ring systems included in the term as designated herein are the following rings wherein X is NR, O or S; and R is H or an optional substituent as described hereinbelow:

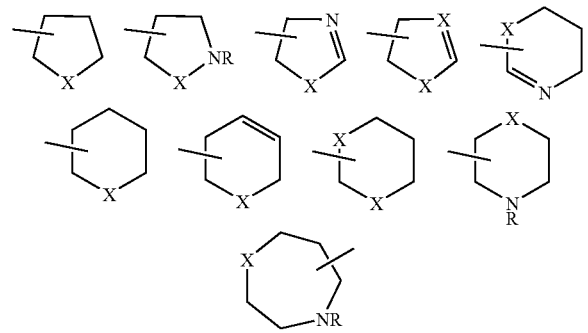

Similarly, as used in the specification and claims, the term heteroaryl designates a five- to ten-membered aromatic ring system containing 1, 2 or 3 heteroatoms, which may be the same or different, selected from N, O or S. Such heteroaryl ring systems include pyrrolyl, azolyl, oxazolyl, thiazolyl, imidazolyl, furyl, thienyl, quinolinyl, isoquinolinyl, indolyl, benzothienyl, benzofuranyl, benzisoxazolyl or the like. The term aryl designates a carbocyclic aromatic ring system such as phenyl, naphthyl, anthracenyl or the like. The term haloalkyl as used herein designates a $C_nH_{2n+1}$ group having from one to 2n+1 halogen atoms which may be the same or different and the term haloalkoxy as used herein designates an $OC_nH_{2n+1}$ group having from one to 2n+1 halogen atoms which may be the same or different.

Exemplary of the 8- to 13-membered bicyclic or tricyclic ring systems having a N atom at the bridgehead and optionally containing 1, 2 or 3 additional heteroatoms selected from N, O or S included in the term as designated herein are the following ring systems wherein $W_2$ is NR, O or S; and R is H or an optional substituent as described hereinbelow:

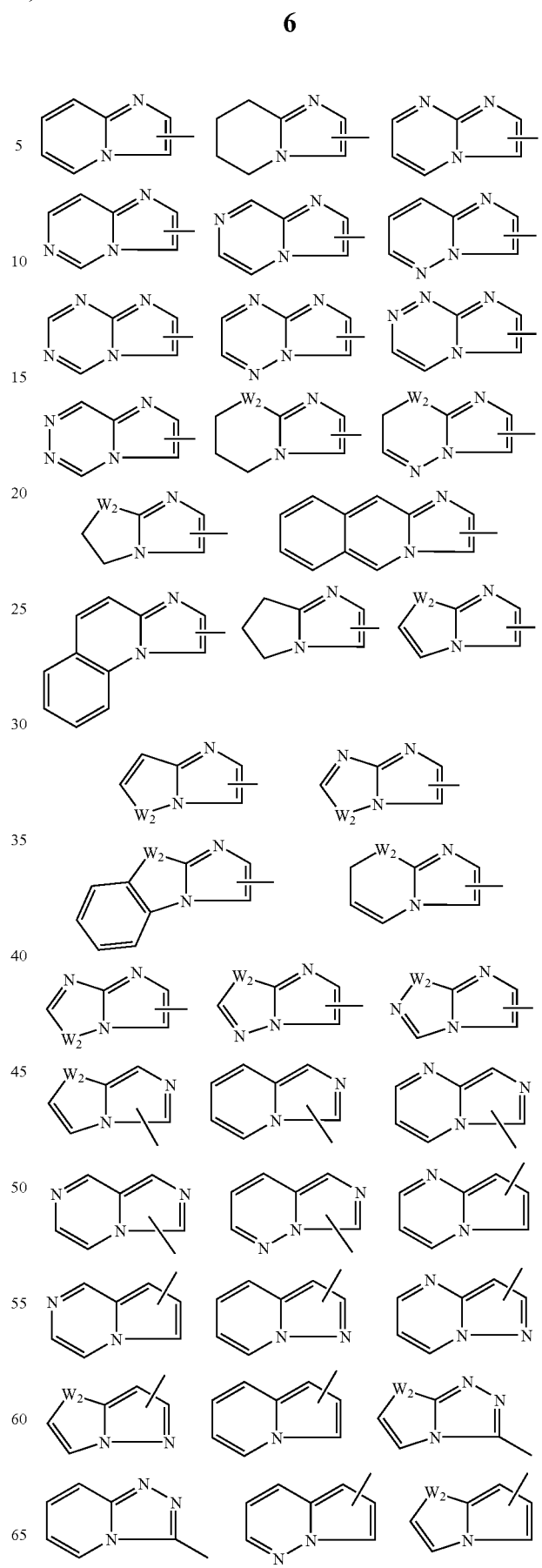

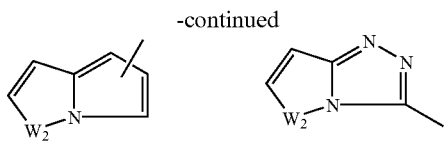

In the specification and claims, when the terms $C_1$–$C_6$alkyl, $C_2$–$C_6$alkenyl, $C_2$–$C_6$alkynyl, $C_3$–$C_7$cycloalkyl, cycloheteroalkyl, aryl or heteroaryl are designated as being optionally substituted, the substituent groups which are optionally present consist of the following halogen atoms, nitro, cyano, thiocyanato, cyanato, hydroxyl, alkyl, haloalkyl, alkoxy, haloalkoxy, amino, alkylamino, dialkylamino, formyl, alkoxycarbonyl, carboxyl, alkanoyl, alkylthio, alkylsuphinyl, alkylsulphonyl, carbamoyl, alkylaminocarbonyl, phenyl, phenoxy, benzyl, benzyloxy, or cycloalkyl groups, preferably halogen atoms or lower alkyl or lower alkoxy groups. Typically, 0–3 substituents may be present. When any of the foregoing substituents represents or contains an alkyl substituent group, this may be linear or branched and may contain up to 12, preferably up to 6, more preferably up to 4 carbon atoms.

Pharmaceutically acceptable salts may be any acid addition salt formed by a compound of formula I and a pharmaceutically acceptable acid such as phosphoric, sulfuric, hydrochloric, hydrobromic, citric, maleic, malonic, mandelic, succinic, fumaric, acetic, lactic, nitric, sulfonic, p-toluene sulfonic, methane sulfonic acid or the like.

Compounds of the invention include esters, carbamates or other conventional prodrug forms, which in general, are functional derivatives of the compounds of the invention and which are readily converted to the inventive active moiety in vivo. Correspondingly, the method of the invention embraces the treatment of the various conditions described hereinabove with a compound of formula I or with a compound which is not specifically disclosed but which, upon administration, converts to a compound of formula I in vivo. Also included are metabolites of the compounds of the present invention defined as active species produced upon introduction of these compounds into a biological system.

Compounds of the invention may exist as one or more stereoisomers. The various stereoisomers include enantiomers, diastereomers, atropisomers and geometric isomers. One skilled in the art will appreciate that one stereoisomer may be more active or may exhibit beneficial effects when enriched relative to the other stereoisomer(s) or when separated from the other stereoisomer(s). Additionally, the skilled artisan knows how to separate, enrich or selectively prepare said stereoisomers. Accordingly, the present invention comprises compounds of formula I, the stereoisomers thereof and the pharmaceutically acceptable salts thereof. The compounds of the invention may be present as a mixture of stereoisomers, individual stereoisomers, or as an optically active or enantiomerically pure form.

Preferred compounds of the invention are those compounds of formula I wherein n is 1. Another group of preferred compounds are those compounds of formula I wherein $R_4$ is H or an optionally substituted $C_1$–$C_4$alkyl group. A further group of preferred compounds of the invention are those compounds of formula I wherein $R_2$ is an optionally substituted phenyl, naphthyl or heteroaryl group. Also preferred are those compounds of formula I wherein $R_5$, $R_6$ and $R_7$ are H.

More preferred compounds of the invention are those compounds of formula I wherein A is N and $R_4$ is H or an optionally substituted $C_1$–$C_4$alkyl group. Another group of more preferred compounds are those compounds of formula I wherein A is N; n is 1 and $R_2$ is an optionally substituted phenyl, naphthyl or heteroaryl group. Further more preferred compounds of the invention are those compounds of formula I wherein the 6- or 7-membered azacyclic ring is attached to the indazole in the 5 or 7 position.

Among the preferred compounds of the invention are:
5-(4-methylpiperazin-1-yl)-3-(1-naphthylsulfonyl)-1H-indazole;
3-(1-naphthylsulfonyl)-5-piperazin-1-yl-1H-indazole;
3-(1-naphthylsulfonyl)-7-piperazin-1-yl-1H-indazole;
1-(3-chlorobenzyl)-5-(4-methylpiperazin-1-yl)-3-(1-naphthylsulfonyl)-1H-indazole;
7-(4-methylpiperazin-1-yl)-3-(phenylsulfonyl)-1H-indazole;
3-(phenylsulfonyl)-7-(4-propylpiperazin-1-yl)-1H-indazole;
3-(phenylsulfonyl)-7-piperazin-1-yl-1H-indazole;
5-(4-methylpiperazin-1-yl)-3-(phenylsulfonyl)-1H-indazole;
3-(phenylsulfonyl)-5-(4-propylpiperazin-1-yl)-1H-indazole;
3-(phenylsulfonyl)-5-piperazin-1-yl-1H-indazole;
5-piperazin-1-yl-3-[(3-cyanophenyl)sulfonyl]-1H-indazole;
7-(4-methylpiperazin-1-yl)-3-[(2-phenethyl)sulfonyl]-1H-indazole;
3-(1-naphthylsulfonyl)-7-(4-propylpiperazin-1-yl)-1H-indazole;
5-(4-phenethylpiperazin-1-yl)-3-(1-naphthylsulfonyl)-1H-indazole;
5-(4-methylpiperazin-1-yl)-3-(2-naphthylsulfonyl)-1H-indazole;
3-[(2-chloro-4-fluorophenyl)sulfonyl]-5-piperazin-1-yl-1H-indazole;
1-methyl-3-(phenylsulfonyl)-5-piperazin-1-yl-1H-indazole;
1-phenyl-3-(phenylsulfonyl)-5-piperazin-1-yl-1H-indazole;
1-methyl-3-(phenylsulfonyl)-7-piperazin-1-yl-1H-indazole;
1-phenyl-3-(phenylsulfonyl)-7-piperazin-1-yl-1H-indazole;
7-piperazin-1-yl-3-[(3-fluorophenyl)sulfonyl]-1H-indazole;
3-[(4-fluorophenyl)sulfonyl]-7-(4-methylpiperazin-1-yl)-1H-indazole;
3-[(2-chlorophenyl)sulfonyl]-7-piperazin-1-yl-1H-indazole;
3-[(4-aminophenyl)sulfonyl]-7-piperazin-1-yl-1H-indazole;
5-piperazin-1-yl-3-[(3-fluorophenyl)sulfonyl]-1H-indazole;
3-[(4-fluorophenyl)sulfonyl]-5-(4-methylpiperazin-1-yl)-1H-indazole;
3-[(2-chlorophenyl)sulfonyl]-5-(4-propylpiperazin-1-yl)-1H-indazole;
3-[(4-aminophenyl)sulfonyl]-5-piperazin-1-yl-1H-indazole;
3-[(5-chlorothien-2-yl)sulfonyl]-5-piperazin-1-yl-1H-indazole;
3-[(5-chlorothien-2-yl)sulfonyl]-7-piperazin-1-yl-1H-indazole;
4-chloro-3-(phenylsulfonyl)-7-piperazin-1-yl-1H-indazole;
5-fluoro-3-(phenylsulfonyl)-7-piperazin-1-yl-1H-indazole;
6-fluoro-3-(phenylsulfonyl)-7-piperazin-1-yl-1H-indazole;
4-chloro-3-(phenylsulfonyl)-5-piperazin-1-yl-1H-indazole;
7-fluoro-3-(phenylsulfonyl)-5-piperazin-1-yl-1H-indazole;
6-fluoro-3-(phenylsulfonyl)-5-piperazin-1-yl-1H-indazole;
6-(4-phenethylpiperazin-1-yl)-3-(phenylsulfonyl)-1H-indazole;
6-(4-methylpiperazin-1-yl)-3-(phenylsulfonyl)-1H-indazole;
6-(4-propylpiperazin-1-yl)-3-(phenylsulfonyl)-1H-indazole;
3-(phenylsulfonyl)-6-piperazin-1-yl-1H-indazole;

4-piperazin-1-yl-3-(phenylsulfonyl)-1H-indazole;
4-(4-methylpiperazin-1-yl)-3-(phenylsulfonyl)-1H-indazole;
4-(4-propylpiperazin-1-yl)-3-(phenylsulfonyl)-1H-indazole;
3-(phenylsulfonyl)-4-piperazin-1-yl-1H-indazole;
3-[(5-chlorothien-2-yl)sulfonyl]-5-piperidin-1-yl-1H-indazole;
3-[(5-chlorothien-2-yl)sulfonyl]-7-piperidin-1-yl-1H-indazole;
1-methyl-3-(phenylsulfonyl)-5-piperidin-1-yl-1H-indazole;
3-[(3-fluorophenyl)sulfonyl]-5-piperidin-1-yl-1H-indazole;
1-methyl-3-(phenylsulfonyl)-7-(4-methylpiperidin-1-yl)-1H-indazole;
3-[(3-fluorophenyl)sulfonyl]-7-piperidin-1-yl-1H-indazole;
3-[(3-fluorophenyl)sulfonyl]-5-piperidin-1-yl-1H-indazole;
3-(phenylsulfonyl)-5-piperidin-1-yl-1H-indazole;
1-methyl-3-[(3-fluorophenyl)sulfonyl]-7-piperidin-1-yl-1H-indazole;
3-(phenylsulfonyl)-7-piperidin-1-yl-1H-indazole;
5-[1,4]diazepan-1-yl-3-(phenylsulfonyl)-1H-indazole;
7-[1,4]diazepan-1-yl-3-(phenylsulfonyl)-1H-indazole;
5-[1,4]diazepan-1-yl-3-(1-naphthylsulfonyl)-1H-indazole;
7-[1,4]diazepan-1-yl-3-(1-naphthylsulfonyl)-1H-indazole;
the stereoisomers thereof; or
the pharmaceutically acceptable salts thereof.

Compounds of the invention may be prepared using conventional synthetic methods and, if required, standard separation or isolation techniques. For example, compounds of formula I wherein A is N; $R_3$ is H; and ----- represents a single bond (Ia) may be prepared by reacting a halonitrobenzene compound of formula II with a chloromethylsulfone of formula III in the presence of strong base, such as KO-t-Bu or KOH, to give the benzylsulfonyl compound of formula IV; reacting said formula IV compound with a piperazine or homopiperazine of formula V in the presence of a base such as $K_2CO_3$ to give the compound of formula VI; reacting said formula VI compound with a reducing agent such as Sn, Fe or Zn in the presence of an acid to give the corresponding amine of formula VII; and reacting said amine with $NaNO_2$ in the presence of an acid to give the desired compound of formula Ia. The reaction is illustrated in flow diagram I wherein Hal represents Cl or F.

FLOW DIAGRAM I

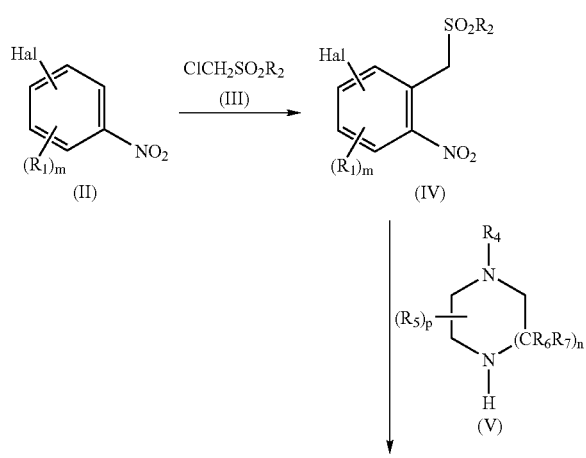

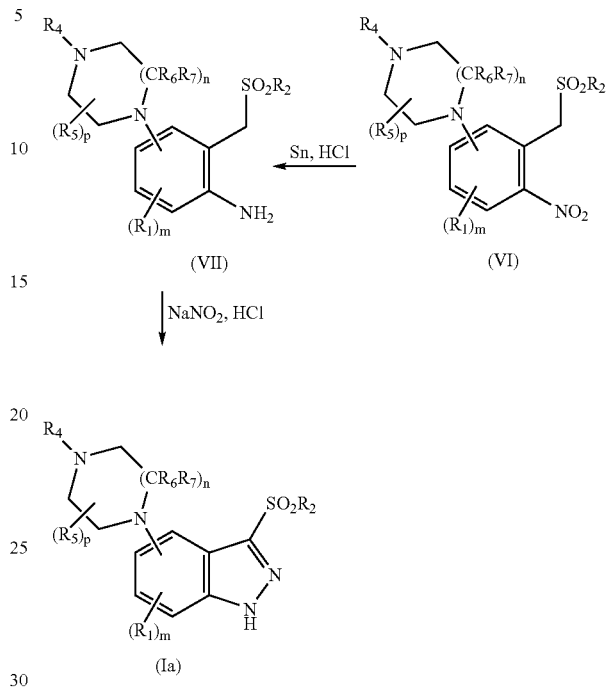

Compounds of formula Ia wherein $R_3$ is other than H may be prepared using conventional alkylation/deprotection procedures. For example, compounds of formula I wherein A is N; $R_3$ is other than H; and ----- represents a single bond (Ib) may be prepared by reacting a protected compound of formula VIII with an alkylating agent of formula IX in the presence of a base and a solvent optionally in the presence of a phase-transfer agent to give the protected alkylated compound of formula X and deprotecting said formula X compound to give the desired compound of formula Ib wherein $R_4$ is H. Alternatively, for those compounds wherein $R_3$ is an aryl or heteroaryl group, the agent of formula IX may be an aryl or heteroaryl boronic acid and may be coupled with the formula VIII indazole in the presence of a catalyst, e.g., $Cu(OCOCH_3)_2$ to give the corresponding protected compound of formula X wherein $R_3$ is an aryl or heteroaryl group. Optionally the formula Ib compound may be reacted with an alkylating agent of formula XI under standard alkylation conditions to give the compound of formula Ib wherein $R_4$ is other than H. If desired, the sequence may be reversed by deprotecting the formula VIII compound to give the compound of formula Ia wherein $R_3$ and $R_4$ are H (Ic) and alkylating the formula Ic compound with the formula XI alkylating agent to give the compound of formula Id. Optionally, the formula Id compound may be reacted with a formula IX alkylating agent, as described hereinabove, to give the compound of formula Ib. The reactions are shown in flow diagram II wherein P is a protecting group and LG is a leaving group such as Cl, Br, I, OH, $B(OH)_2$, tosyl, mesyl or the like.

FLOW DIAGRAM II

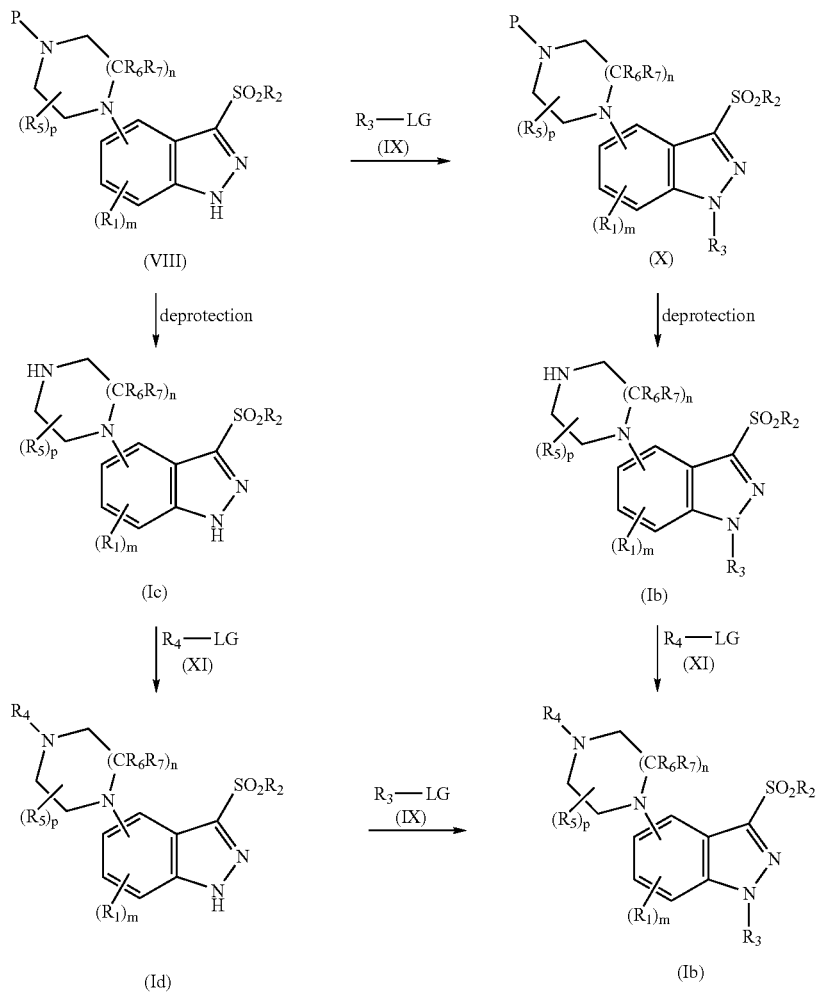

Alternatively, compounds of formula Ib may be prepared directly from an indazole compound of formula XII by coupling said formula XII compound with the appropriate piperazine or homopiperazine compound of formula V in the presence of a catalyst such as a palladium or nickel catalyst. The reaction is shown in flow diagram III wherein LG' is a leaving group such as Cl, Br, I or an activated hydroxyl group such as $CF_3SO_3$ (triflate).

FLOW DIAGRAM III

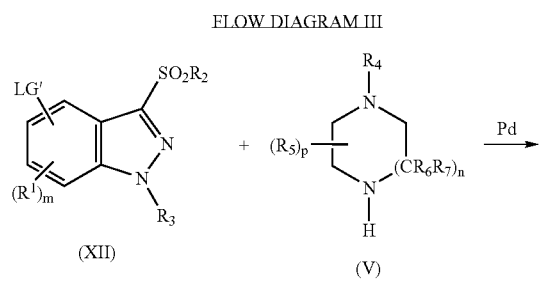

-continued

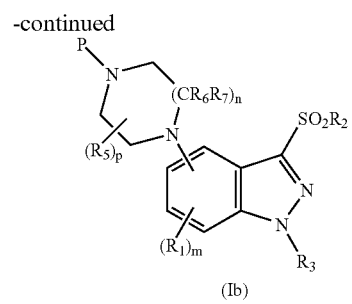

Compounds of formula VIII may also be prepared by reacting a protected 3-iodoindazole of formula XIII with a sodium sulfinate of formula XIV in the presence of copper iodide and dimethyl formamide (DMF) to give the desired compound of formula VIII or by reacting the formula XIII compound with a thiol of formula XV in the presence of copper iodide and a base, such as $K_2CO_3$, to give the thio ether of formula XVI and oxidizing said formula XVI compound to give the desired compound of formula VIII. The reactions are shown in flow diagram IV wherein P represents a protecting group.

FLOW DIAGRAM IV

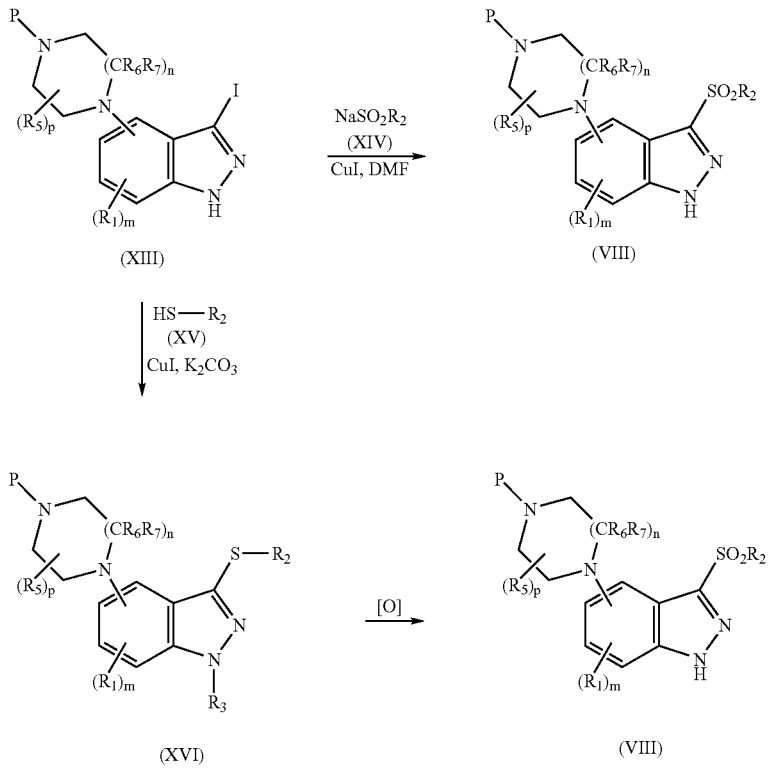

Compounds of formula XIII wherein $R_1$ is H (XIIIa) may be prepared by reacting a dihalobenzaldehyde of formula XVII with the piperazine or homopiperazine compound of formula V wherein R4 is a protecting group (Va) to give the ortho halobenzaldehyde compound of formula XVIII, reacting the formula XVIII compound with hydrazine hydrate to give the indazole of formula XIX and reacting the formula XIX indazole with iodine in the presence of a base, such as KOH, to give the desired formula XIIIa compounds. The reactions are shown in flow diagram V wherein P is a protecting group and Hal is F, Cl, Br, or I, preferably F.

FLOW DIAGRAM V

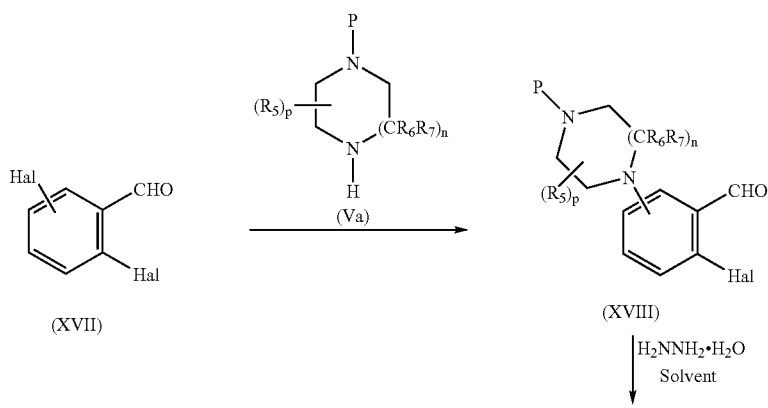

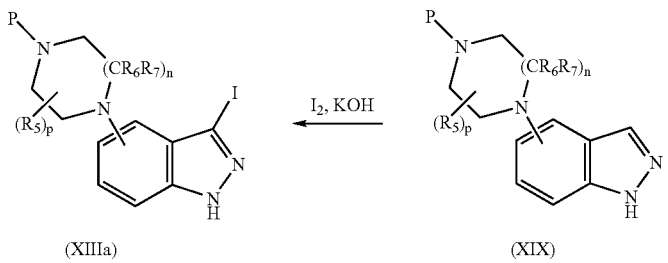

(XIIIa)          (XIX)

Compounds of formula XIII wherein n is 1 and $R_5$, $R_6$ and $R_7$ are H (XIIIb) may be prepared by reacting an indazole amine of formula XX with di(2-chloroethyl)amine hydrochloride to give the corresponding piperazinyl indazole of formula XXI, protecting said formula XXI compound and reacting the protected formula XXI compound with iodine in the presence of a base, such as KOH, to give the desired compound of formula XIIIb. The reactions are shown in flow diagram VI whereing P represents a protecting group.

Compounds of XIIIa and XIIIb may be converted to compounds of formula Ia, Ib, or Ic as shown hereinabove in flow diagrams II and III.

Corresponding compounds of the invention wherein A is $CR_8$ may be obtained, for example, by lithiating a protected bromoindazole of formula XXII, and reacting the lithiated compound in situ with an N-protected azacyclic ketone of formula XXIII to give the protected hydroxy compound of formula XXIV, said hydroxy compound may then be dehy-

FLOW DIAGRAM VI

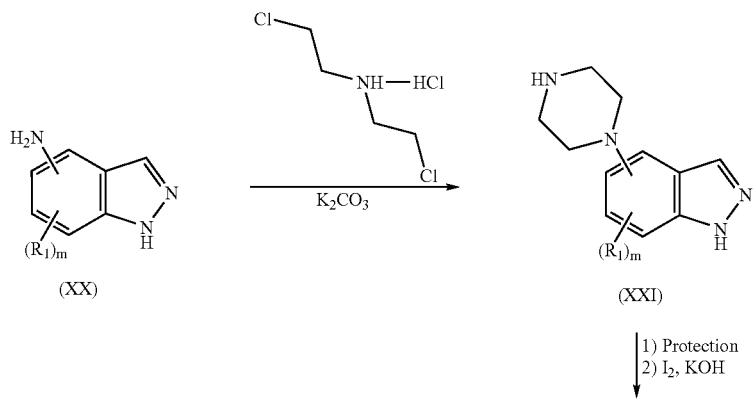

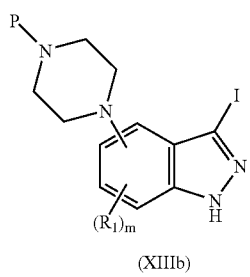

(XIIIb)

drated to give the protected compound of formula XXV. Catalytic hydrogenation and subsequent deprotection of said formula XXV compound gives the desired compounds of formula I wherein A is $CR_8$; $R_3$ and $R_4$ are H; and ----- represents a single bond (Id). The reaction sequence is shown in flow diagram VII wherein P and P' each independently represent a protecting group.

Alternatively, compounds of formula I wherein A is C or $CR_8$ and $R_3$ is H (Ie) may be prepared by reacting a chloromethylsulfonyl compound of formula III with a nitrobenzene derivative of formula XXVI in the presence of a strong base, such as KO-t-Bu or KOH, to provide the compound of formula XXVII; reducing said formula XVII compound with a reducing agent such as Sn, Fe or Zn in the

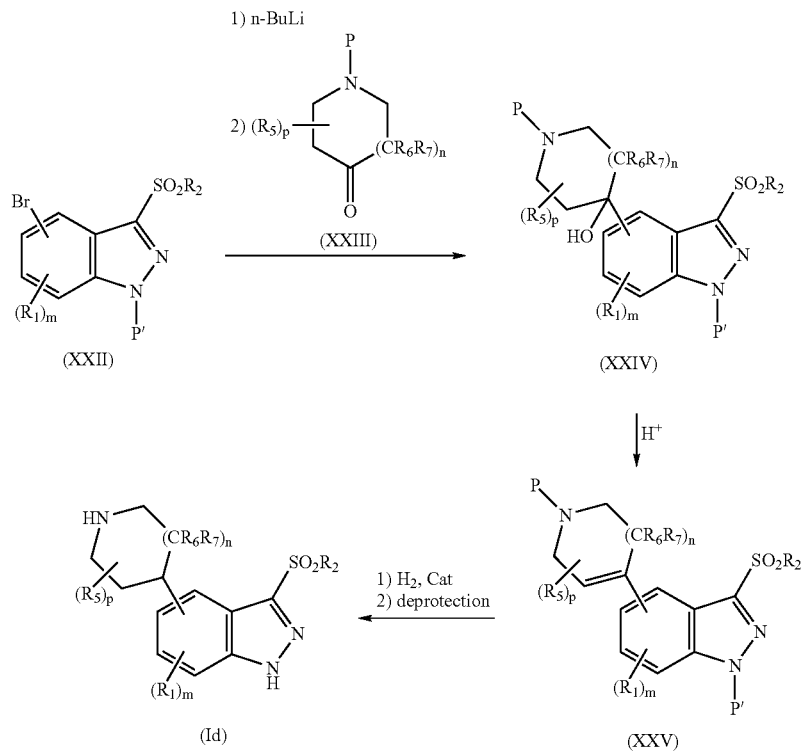

Using the procedures shown in flow diagram II hereinabove, the compounds of formulas XXIV, XXV and Id may be readily converted to compounds of formula I wherein A is $CR_8$ and $R_3$ or $R_4$ are other than H.

presence of an acid to give the corresponding amine of formula XXVIII; and reacting said amine with $NaNO_2$ in the presence of an acid to give the desired indazole compound of formula Ie. The reactions are shown in flow diagram VIII.

FLOW DIAGRAM VIII

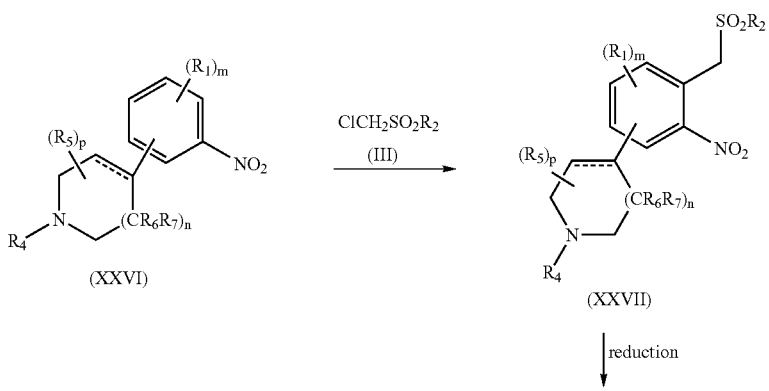

-continued

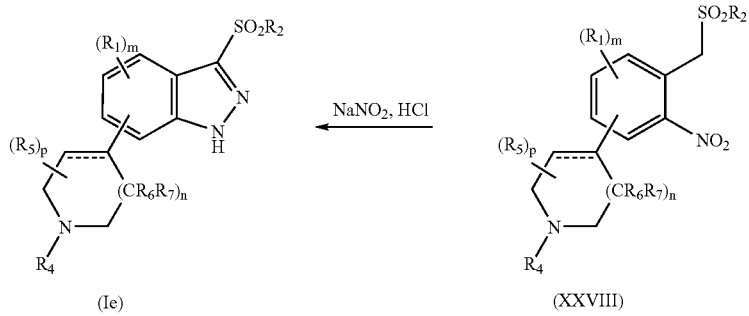

(Ie) ← NaNO$_2$, HCl ← (XXVIII)

Compounds of formula Ie may be converted to the corresponding compounds of formula I wherein A is C or CR$_8$ and R$_3$ is other than H by reacting said formula Ie compound with an alkylating agent as shown hereinabove in flow diagram II.

Protecting groups suitable for use in the reactions shown hereinabove include t-butyloxycarbonyl, benzyl, acetyl, benzyloxycarbonyl, or any conventional group known to protect a basic nitrogen in standard synthetic procedures.

Advantageously, the formula I compounds of the invention are useful for the treatment of CNS disorders relating or affected by 5-HT6 receptor including motor, mood, personality, behavioral, psychiatric, cognitive, neurodegenerative, or the like disorders, for example Alzheimer's disease, Parkinson's disease, attention deficit disorder, anxiety, epilepsy, depression, obsessive compulsive disorder, sleep disorders, neurodegenerative disorders (such as head trauma or stroke), feeding disorders (such as anorexia or bulimia), schizophrenia, memory loss, disorders associated with withdrawal from drug or nicotine abuse, or the like or certain gastrointestinal disorders such as irritable bowel syndrome. Accordingly, the present invention provides a method for the treatment of a disorder of the central nervous system related to or affected by the 5-HT6 receptor in a patient in need thereof which comprises providing said patient a therapeutically effective amount of a compound of formula I as described hereinabove. The compounds may be provided by oral or parenteral administration or in any common manner known to be an effective administration of a therapeutic agent to a patient in need thereof.

The term "providing" as used herein with respect to providing a compound or substance embraced by the invention, designates either directly administering such a compound or substance, or administering a prodrug, derivative or analog which forms an equivalent amount of the compound or substance within the body.

The therapeutically effective amount provided in the treatment of a specific CNS disorder may vary according to the specific condition(s) being treated, the size, age and response pattern of the patient, the severity of the disorder, the judgment of the attending physician or the like. In general, effective amounts for daily oral administration may be about 0.01 to 1,000 mg/kg, preferably about 0.5 to 500 mg/kg and effective amounts for parenteral administration may be about 0.1 to 100 mg/kg, preferably about 0.5 to 50 mg/kg.

In actual practice, the compounds of the invention are provided by administering the compound or a precursor thereof in a solid or liquid form, either neat or in combination with one or more conventional pharmaceutical carriers or excipients. Accordingly, the present invention provides a pharmaceutical composition which comprises a pharmaceutically acceptable carrier and an effective amount of a compound of formula I as described hereinabove.

Solid carriers suitable for use in the composition of the invention include one or more substances which may also act as flavoring agents, lubricants, solubilizers, suspending agents, fillers, glidants, compression aides, binders, tablet-disintegrating agents or encapsulating materials. In powders, the carrier may be a finely divided solid which is in admixture with a finely divided compound of formula I. In tablets, the formula I compound may be mixed with a carrier having the necessary compression properties in suitable proportions and compacted in the shape and size desired. Said powders and tablets may contain up to 99% by weight of the formula I compound. Solid carriers suitable for use in the composition of the invention include calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Any pharmaceutically acceptable liquid carrier suitable for preparing solutions, suspensions, emulsions, syrups and elixirs may be employed in the composition of the invention. Compounds of formula I may be dissolved or suspended in a pharmaceutically acceptable liquid carrier such as water, an organic solvent, or a pharmaceutically acceptable oil or fat, or a mixture thereof. Said liquid composition may contain other suitable pharmaceutical additives such as solubilizers, emulsifiers, buffers, preservatives, sweeteners, flavoring agents, suspending agents, thickening agents, coloring agents, viscosity regulators, stabilizers, osmo-regulators, or the like. Examples of liquid carriers suitable for oral and parenteral administration include water (particularly containing additives as above, e.g., cellulose derivatives, preferably sodium carboxymethyl cellulose solution), alcohols (including monohydric alcohols and polyhydric alcohols, e.g., glycols) or their derivatives, or oils (e.g., fractionated coconut oil and arachis oil). For parenteral administration the carrier may also be an oily ester such as ethyl oleate or isopropyl myristate.

Compositions of the invention which are sterile solutions or suspensions are suitable for intramuscular, intraperitoneal or subcutaneous injection. Sterile solutions may also be administered intravenously. Inventive compositions suitable for oral administration may be in either liquid or solid composition form.

For a more clear understanding, and in order to illustrate the invention more clearly, specific examples thereof are set forth hereinbelow. The following examples are merely illustrative and are not to be understood as limiting the scope and underlying principles of the invention in any way.

Unless otherwise stated, all parts are parts by weight. The term NMR designates proton nuclear magnetic resonance. The terms THF, DMF and DMSO designate tetrahydrofuran, dimethyl formamide and dimethylsulfoxide, respectively. In the chemical drawings, the term Ph represents a phenyl group.

EXAMPLE 1

Preparation of 1-Benzyl-4-(4-nitrophenyl)piperazine

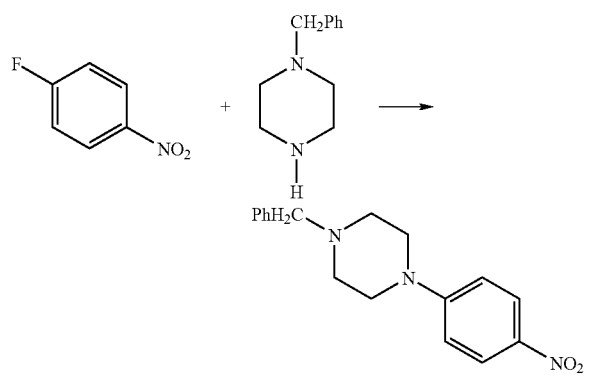

A stirred solution of 1-benzylpiperazine (8.81 g, 50.0 mmol), 4-fluoronitrobenzene (5.31 mL, 50.0 mmol), and $K_2CO_3$ (6.90 g, 50.0 mmol) in ethanol is heated at reflux temperature under nitrogen for 18 h, cooled, diluted with water, and extracted with $CH_2Cl_2$. The combined extracts are dried over $MgSO_4$ and concentrated in vacuo to give a solid residue. The solid is triturated with 20:80 ethyl acetate: hexanes and filtered. The filtercake is air-dried to afford the title compound as orange crystals, 8.45 g (57% yield), mp 218–219° C., characterized by NMR and mass spectral analyses.

EXAMPLE 2

Preparation of 1-Benzyl-4-{4-nitro-3-[(phenylsulfonyl)methyl]phenyl}piperazine

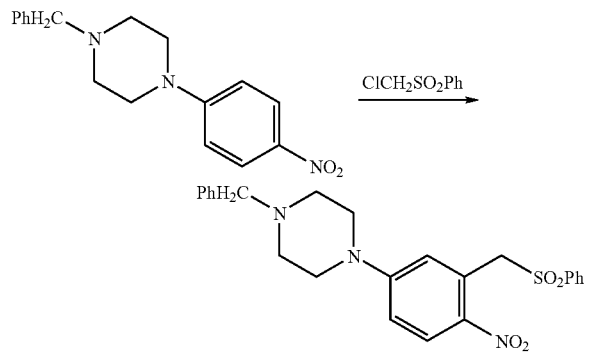

A stirred solution of 1-benzyl-4-(4-nitrophenyl)piperazine (5.95 g, 20.0 mmol) and chloromethylphenylsulfone (3.82 g, 20.0 mmol) in dry THF under nitrogen at −60° C. is treated with 1.0M KO-t-Bu in THF (44.0 mL, 44.0 mmol), warmed to −20° C. over a 1 h period, quenched with acetic acid and treated sequentially with water, saturated aqueous $NaHCO_3$ and ether. The phases are separated and the aqueous phase is extracted with ether. The combined ethers are washed with water and brine, dried over $MgSO_4$ and concentrated in vacuo. The resultant residue is chromatographed (silica gel, 1:1 and 1:0 ethyl acetate:hexanes as eluent) to give the title compound as a yellow solid, 7.52 g (83% yield), mp 145–146° C., characterized by NMR and mass spectral analyses.

EXAMPLE 3

Preparation of 4-(4-Benzylpiperazin-1-yl)-2-[(Phenylsulfonyl)methyl]aniline

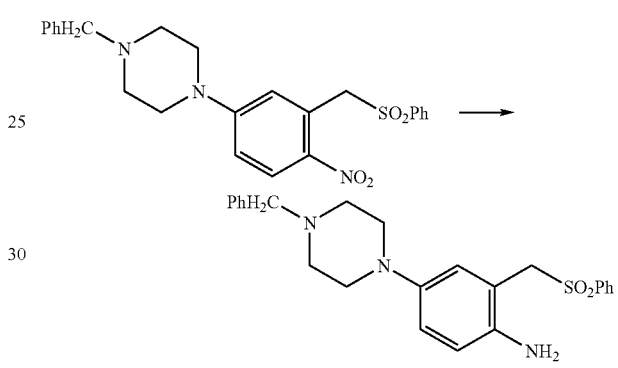

A mixture of 1-benzyl-4-{4-nitro-3-[(phenylsulfonyl)methyl]phenyl}piperazine (6.77 g, 15.0 mmol) and granular tin (7.48 g, 63.0 mmol) in methanol and conc. hydrochloric acid is heated at 45° C. for 4 h, stirred at ambient temperature for 18 h, carefully poured into saturated aqueous $NaHCO_3$, treated with ether and stirred for 0.5 h. The phases are separated and the aqueous phase is extracted sequentially with ether and $CH_2Cl_2$. The extracts and organic phase are combined, dried over $MgSO_4$ and concentrated in vacuo. The resultant residue is dissolved in $CH_2Cl_2$ and filtered through Celite®. The filtrate is concentrated in vacuo to afford the title compound as a pale yellow solid, 6.11 g (97% yield), mp 141–143° C., characterized by NMR and mass spectral analyses

EXAMPLE 4

Preparation of 5-(4-Benzylpiperazin-1-yl)-3-(phenylsulfonyl)-1H-indazole hydrochloride

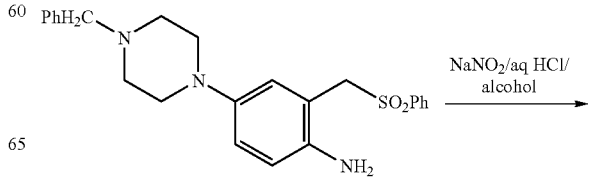

-continued

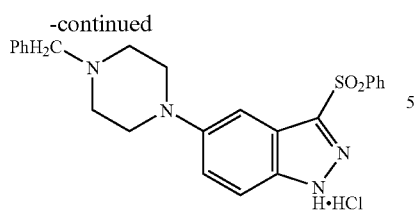

A stirred solution of 4-(4-benzylpiperazin-1-yl)-2-[(phenylsulfonyl)methyl]-aniline (0.371 g, 0.88 mmol) in 4.0 M aqueous hydrochloric acid is cooled in an ice bath, treated dropwise with $NaNO_2$ (91 mg, 1.32 mmol) in water, stirred for 40 min, treated with 2.5 M aqueous NaOH to pH ~14 and filtered. The filtercake is dissolved in $CH_2Cl_2$, and chromatographed (silica gel, ethyl acetate as eluent) to afford the free indazole of the title product as a yellow solid (276 mg, 64%). The solid is dissolved in a mixture of ethanol and $CH_2Cl_2$, treated with 4.0 M HCl in dioxane, and concentrated in vacuo to give a solid residue. The residue is triturated with ethyl acetate to afford the title product as an off-white solid, 278 mg (57% yield), mp 177–180° C., identified by NMR and mass spectral analyses.

EXAMPLE 5

Preparation of 5-(4-Benzylpiperazin-1-yl)-3-[(3-fluorophenyl)sulfonyl]-1H-indazole hydrochloride

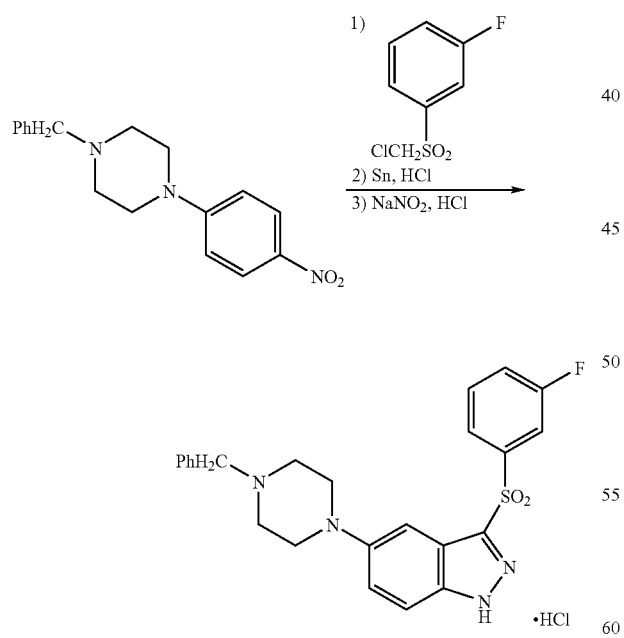

Using essentially the same procedures described hereinabove for Examples 2–4 and employing chloromethyl-(3-fluorophenyl)sulfone, the title compound is obtained as an off-white solid, mp 157–160° C., identified by NMR and mass spectral analyses.

EXAMPLE 6

Preparation of 1-Benzyl-4-(3-methoxy-4-nitrophenyl)piperazine

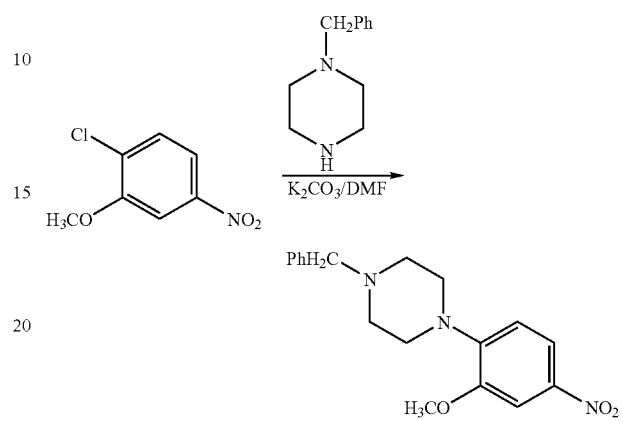

A stirred solution of 1-benzylpiperazine (3.53 g, 20.0 mmol), 4-chloro-3-methoxy-nitrobenzene (3.75 g, 20.0 mmol), and $K_2CO_3$ (2.76 g, 20.0 mmol) in DMF is heated at 850 to 100° C. under nitrogen for 23 h, cooled to room temperature, treated with 2M aqueous hydrochloric acid, diluted with water and extracted with ether. The combined extracts are washed with brine, dried over $MgSO_4$ and concentrated in vacuo. The resultant residue is chromatographed (silica gel, 30:70 ethyl acetate:hexanes and 50:50 ethyl acetate:hexanes as eluent) to afford the title compound as a yellow-orange oil 2.64 g (57% yield), identified by NMR analysis.

EXAMPLE 7

Preparation of 5-(4-Benzylpiperazin-1-yl)-6-methoxy-3-(phenylsulfonyl)-1H-indazole hydrochloride

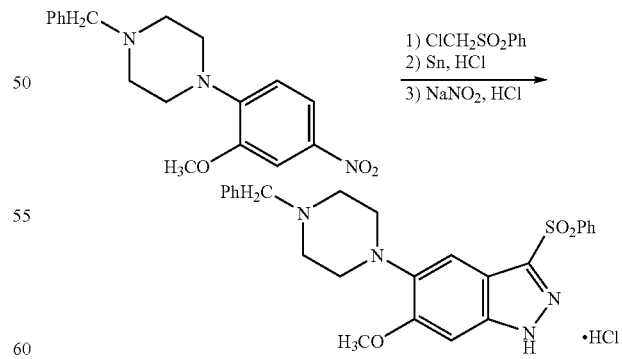

Using essentially the same procedures described hereinabove for Examples 2–4 and employing 1-benzyl-4-(2-methoxy-4-nitrophenyl)piperazine as starting substrate, the title compound is obtained as a tan solid, 70 mg, mp 185–187° C., identified by NMR and mass spectral analyses.

EXAMPLE 8

Preparation of 5-(4-Benzylpiperazin-1-yl)-6-methoxy-1-phenyl-3-(phenyl-sulfonyl)-1H-indazole hydrochloride

EXAMPLE 9

Preparation of 6-Methoxy-1-phenyl 3-(phenylsulfonyl)-5-piperazin-1-yl-1H-indazole hydrochloride

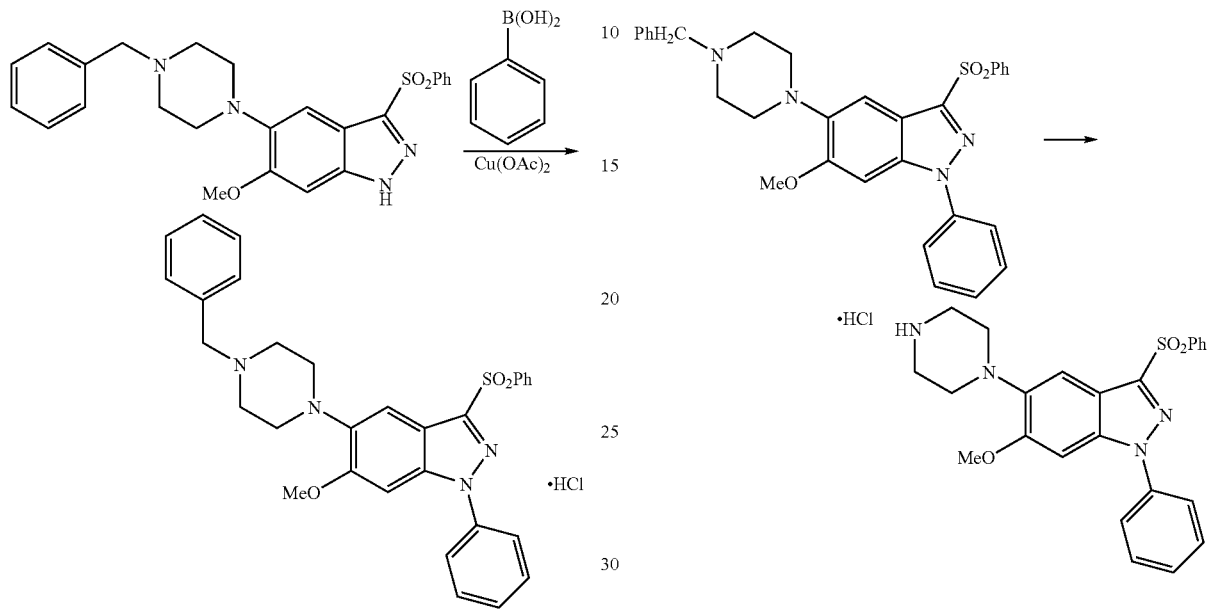

A mixture of 5-(4-benzylpiperazin-1-yl)-6-methoxy-3-(phenylsulfonyl)-1H-indazole (448 mg, 0.97 mmol), phenylboronic acid (242 mg, 1.94 mmol), copper(II) acetate (271 mg, 1.50 mmol), pyridine (160 mg, 2.00 mmol) and 4 Å molecular sieves (1.0 g) in methylene chloride is stirred at room temperature for 48 h and filtered. The filtercake is washed with THF. The filtrates are combined and concentrated in vacuo. The resultant residue is chromatographed (silica gel, 60:40 and 80:20 ethyl acetate:hexanes as eluents) to afford the free amine of the title product as a white solid, 130 mg (25% yield). The free amine is dissolved in ethanol, treated with 4.0 M HCl in dioxane, and concentrated in vacuo to a solid residue. This solid is triturated with ethyl acetate to afford the title product as a white solid, mp: 210–212° C., identified by NMR and mass spectral analyses.

A mixture of 5-(4-benzylpiperazin-1-yl)-6-methoxy-1-phenyl-3-(phenyl-sulfonyl)-1H-indazole (190 mg, 0.353 mmol) and 1-chloroethylchloroformate (250 mg, 1.77 mmol) in 1,2-dichloroethane is heated at reflux temperature for 4 h, cooled to room temperature and concentrated to dryness. The resultant residue is dissolved in ethanol, heated at reflux temperature for 16 h and concentrated in vacuo to give the title compound as a white solid, 130 mg, (82% yield). This compound is purified by recrystalization from ethanol/ether to afford a white solid, mp 167–170° C., identified by NMR and mass spectral analyses.

EXAMPLE 10

Preparation of 6-Methoxy-3-(phenylsulfonyl)-5-(piperazin-1-yl)-1-[4-(trifluoromethyl)phenyl]-1H-indazole hydrochloride

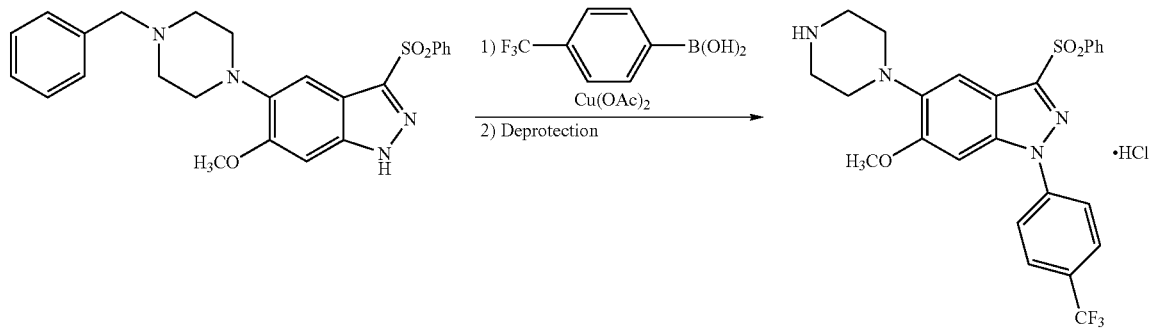

Using essentially the same procedures described in Examples 8 and 9 hereinabove and employing 4-(trifluoromethyl)phenyl boronic acid, the title product is obtained as a white solid, mp 175–177° C., identified by NMR and mass spectral analyses.

EXAMPLE 11

Preparation of 5-(4-Benzylpiperazin-1-yl)-1-methyl-3-(phenylsulfonyl)-1H-indazole

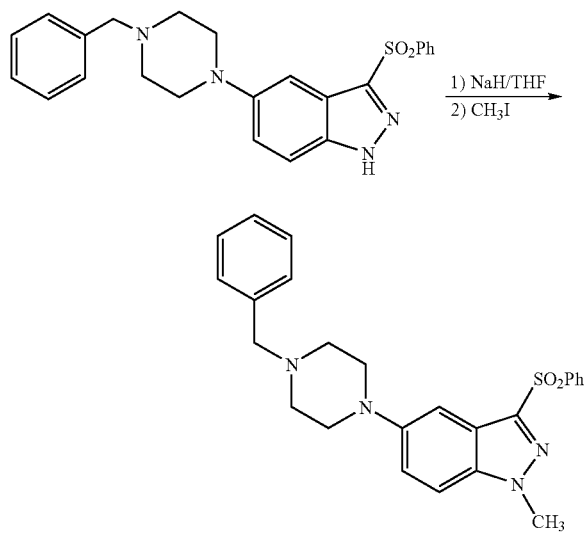

A solution of 5-(4-benzylpiperazin-1-yl)-3-(phenylsulfonyl)-1H-indazole (433 mg, 1.00 mmol) in THF at room temperature is treated with NaH (80 mg, 60% in mineral oil, 2.00 mmol), stirred for 0.5 h, treated with methyl iodide (142 mg, 1.00 mmol), stirred for 16 h, and diluted with water and EtOAc. The organic phase is separated, dried over MgSO$_4$, and concentrated in vacuo. The resultant residue is chromatographed (SiO$_2$, 90:10 EtOAc:hexanes as eluent) to afford the title compound as a white solid, 190 mg (43% yield), mp 195–197° C., identified by mass spectral and NMR analyses.

EXAMPLE 12

Preparation of 5-(4-Benzylpiperazin-1-yl)-1-ethyl-3-(phenylsulfonyl)-1H-indazole dihydrochloride

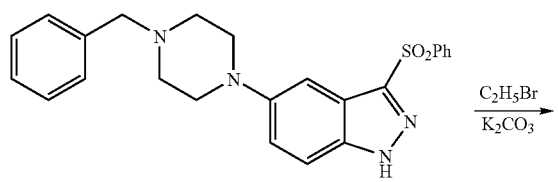

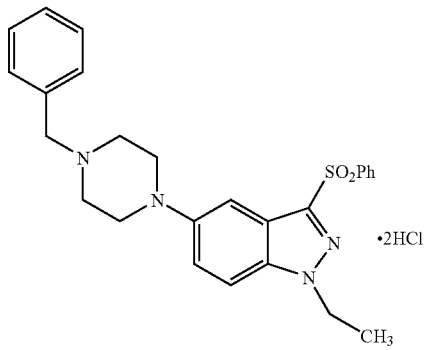

A mixture of 5-(4-benzylpiperazin-1-yl)-3-(phenylsulfonyl)-1H-indazole (400 mg, 0.92 mmol), bromoethane (108 mg, 1.00 mmol) and K$_2$CO$_3$ (276 mg, 2.00 mmol) in DMF is stirred for 16 h at room temperature and diluted water and EtOAc. The organic phase is separated, dried over MgSO$_4$, and concentrated in vacuo. The resultant residue is chromatographed (SiO$_2$, 80:20, then 90:10 EtOAc:hexanes as eluent) to afford the free amine of the title product as a white solid, 230 mg. A portion of this solid (115 mg, 0.25 mmol) is dissolved in ethanol, treated with 4M HCl in dioxane and concentrated in vacuo to give the title compound as a white solid, mp>250° C., identified by mass spectral and NMR analyses.

EXAMPLES 13–93

Preparation of 3-Arylsulfonyl-5-piperazinylindazole Derivatives

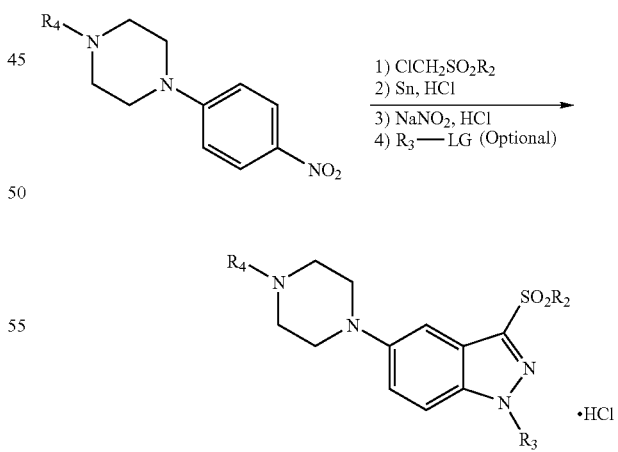

Using essentially the same procedures described in Examples 2–12 hereinabove and employing the appropriate 4-nitrophenylpiperazine as substrate and suitable chloromethylarylsulfone as reactant, the compounds shown on Table I are obtained and identified by HNMR and mass spectral analyses.

TABLE I

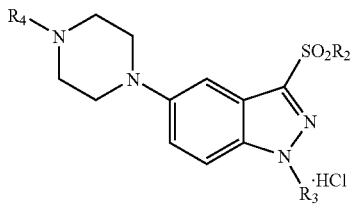

| Ex No | R2 | R3 | R4 | mp ° C. |
|---|---|---|---|---|
| 13 | phenyl | H | methyl | >250 |
| 14 | 1-naphthyl | H | methyl | >250 |
| 15 | 5-chlorothien-2-yl | H | methyl | >250** |
| 16 | phenyl | H | methyl | 208–210 |
| 17 | 4-bromophenyl | H | methyl | >250** |
| 18 | 2-fluorophenyl | H | methyl | 160–161 |
| 19 | 3-fluorophenyl | H | methyl | >250 |
| 20 | phenyl | phenyl | benzyl | 148–151 |
| 21 | phenyl | 4-trifluoromethylphenyl | benzyl | 169–171 |
| 22 | phenyl | 4-ethoxyphenyl | benzyl | 140–144 |
| 23 | phenyl | 3-fluorophenyl | benzyl | 146–149 |
| 24 | phenyl | 3-methoxyphenyl | benzyl | 135–138 |
| 25 | phenyl | 4-fluorophenyl | benzyl | 206–208 |
| 26 | phenyl | 3-chloro-4-fluorophenyl | benzyl | 157–161 |
| 27 | phenyl | 4-methylthiophenyl | benzyl | 156–160 |
| 28 | phenyl | 3-trifluoromethylphenyl | benzyl | 146–150 |
| 29 | phenyl | 3,4-dimethoxyphenyl | benzyl | >200 |
| 30 | phenyl | 4-iodophenyl | benzyl | 196–199 |
| 31 | phenyl | 2-phenethyl | H | 127–130 |
| 32 | phenyl | phenyl | H | >200 |
| 33 | phenyl | 4-trifluoromethylphenyl | H | 170–172 |
| 34 | phenyl | 4-ethoxyphenyl | H | >200 |
| 35 | phenyl | 3-fluorophenyl | H | 139–142 |
| 36 | phenyl | 3-methoxyphenyl | H | 132–135 |
| 37 | phenyl | 4-fluorophenyl | H | 159–161 |
| 38 | phenyl | 3-chloro-4-fluorophenyl | H | >200 |
| 39 | phenyl | 4-methylthiophenyl | H | 160–164 |
| 40 | phenyl | 3-trifluoromethylphenyl | H | 139–142 |
| 41 | phenyl | 3,4-dimethoxyphenyl | H | 156–158 |
| 42 | phenyl | 4-iodophenyl | H | >200 |
| 43 | phenyl | ethyl | H | >200 |
| 44 | phenyl | methyl | H | >200 |
| 45 | 1-naphthyl | 1-propyl | methyl | ** |
| 46 | 1-naphthyl | ethyl | methyl | ** |
| 47 | 1-naphthyl | methyl | methyl | ** |
| 48 | 1-naphthyl | 1-butyl | methyl | ** |
| 49 | 1-naphthyl | 3-chlorobenzyl | methyl | ** |
| 50 | 1-naphthyl | 2-propyl | methyl | ** |
| 51 | 1-naphthyl | 1-(2-methylpropyl) | methyl | ** |
| 52 | 1-naphthyl | benzyl | methyl | ** |
| 53 | 1-naphthyl | H | H | — |
| 54 | 2-thienyl | H | methyl | ** |
| 55 | 3-methylphenyl | H | methyl | ** |
| 56 | 4-methylphenyl | H | methyl | ** |
| 57 | benzyl | H | methyl | ** |
| 58 | 2-fluorophenyl | H | methyl | ** |
| 59 | 3-fluorophenyl | H | methyl | ** |
| 60 | 4-fluorophenyl | H | methyl | ** |
| 61 | 3-cyanophenyl | H | methyl | ** |
| 62 | 4-cyanophenyl | H | methyl | ** |
| 63 | 3-methoxyphenyl | H | methyl | ** |
| 64 | 4-methoxyphenyl | H | methyl | ** |
| 65 | 2-chlorophenyl | H | methyl | ** |
| 66 | 3-chlorophenyl | H | methyl | ** |
| 67 | 4-chlorophenyl | H | methyl | ** |
| 68 | 2,4-difluorophenyl | H | methyl | ** |
| 69 | 3,4-difluorophenyl | H | methyl | ** |

TABLE I-continued

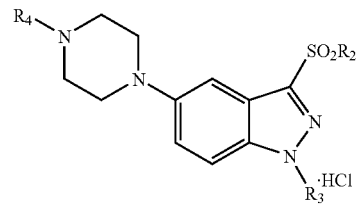

| Ex No | R2 | R3 | R4 | mp ° C. |
|---|---|---|---|---|
| 70 | 5-chlorothien-2-yl | H | methyl | ** |
| 71 | 4-isopropylphenyl | H | methyl | ** |
| 72 | 2-naphthyl | H | methyl | ** |
| 73 | 3-chloro-4-fluorophenyl | H | methyl | ** |
| 74 | 4-n-butylphenyl | H | methyl | ** |
| 75 | 4-t-butylphenyl | H | methyl | ** |
| 76 | 4-aminophenyl | H | methyl | ** |
| 77 | 5-chloro-2-methoxyphenyl | H | methyl | ** |
| 78 | 2,5-dichlorophenyl | H | methyl | ** |
| 79 | 3,5-dichlorophenyl | H | methyl | ** |
| 80 | 4-methylsulfonylphenyl | H | methyl | ** |
| 81 | 4-bromophenyl | H | methyl | ** |
| 82 | 3,5-bis(trifluoromethyl)phenyl | H | methyl | ** |
| 83 | 2-methylphenyl | H | methyl | ** |
| 84 | 2-cyanophenyl | H | methyl | ** |
| 85 | 4-n-propylphenyl | H | methyl | ** |
| 86 | 3-(difluoromethoxy)phenyl | H | methyl | ** |
| 87 | 4-acetylphenyl | H | methyl | ** |
| 88 | 2,3,4-trifluorophenyl | H | methyl | ** |
| 89 | 2-bromophenyl | H | methyl | ** |
| 90 | 2,4,5-trichlorophenyl | H | methyl | ** |
| 91 | 2,6-dichlorophenyl | H | methyl | ** |
| 92 | 2,5-dichlorothien-3-yl | H | methyl | ** |
| 93 | 2-propyl | H | methyl | ** |

**Free Amine

EXAMPLE 94

Preparation of 1-(5-Chloro-2-nitrophenyl)-4-methylpiperazine

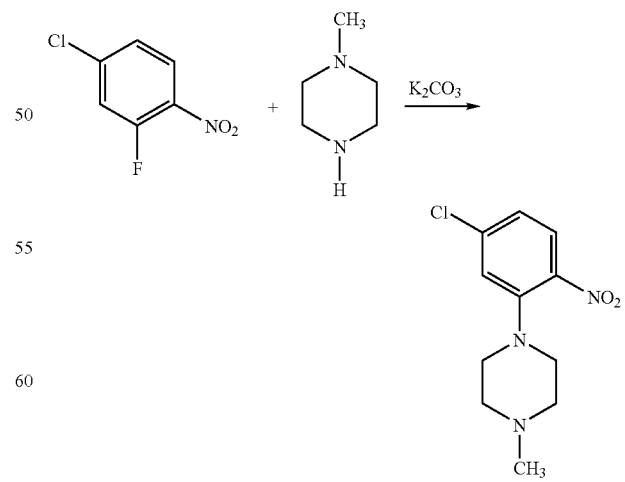

A mixture of 4-chloro-2-fluoro-nitrobenzene (28.5 mmol), 1-methylpiperazine (28.5 mmol) and K$_2$CO$_3$ (37.0 mmol) in DMF is stirred at 100° C. for 16 h and diluted with water and EtOAc. The phases are separated and the aqueous phase is extracted with EtOAc. The organic phase and the extracts are combined, washed sequentially with water and brine, dried over Na₂SO₄ and dried in vacuo. The resultant residue is chromatographed (silica gel, 10% methanol in EtOAc as eluent) to afford the title product.

EXAMPLE 95

Preparation of 1-{5-Chloro-2-nitro-3-{[(4-fluorophenyl)sulfonyl]methyl}phenyl}-4-methylpiperazine

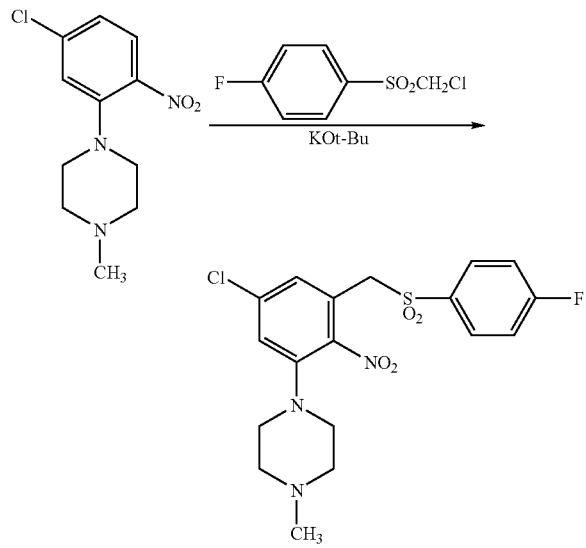

A stirred mixture of 1-(5-chloro-2-nitrophenyl)-4-methylpiperazine (1.0 mmol) and chloromethyl-(4-fluorophenyl) sulfone (1.0 mmol) in THF is treated with 2.2 mL of a 1M KOt-Bu (2.2 mmol) solution in THF at −78° C., warmed to room temperature over a 2 h period, quenched with acetic acid and concentrated in vacuo. The resultant residue is partitioned between EtOAc and aqueous Na₂CO₃. The phases are separated and the aqueous phase is extracted with EtOAc. The organic phase is combined with the extracts, dried over Na₂SO₄ and concentrated to dryness in vacuo to afford the title product.

EXAMPLE 96

Preparation of 4-Chloro-2-{[(4-fluorophenyl)sulfonyl]methyl}-6-(4-methylpiperazin-1-yl)aniline

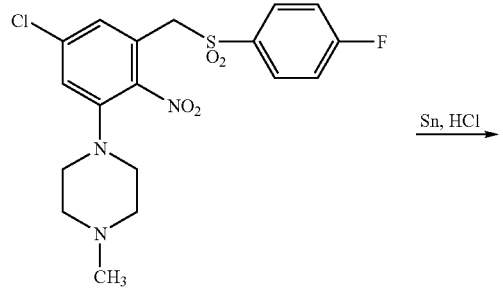

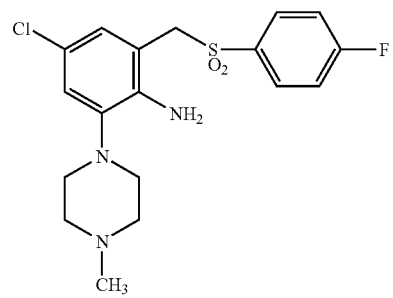

A solution of 1-{5-chloro-2-nitro-3-{[(4-fluorophenyl)sulfonyl]methyl}phenyl}-4-methylpiperazine (1.0 mmol) in methanol is treated with Sn foil (593.3 mg), followed by 5.8 mL of 12 M HCl, heated at 60° C. for 4 h (until reaction is complete by thin layer chromatography), cooled to 0° C., treated with solid NaOH to pH>10 and extracted with CH₂Cl₂. The extracts are combined, washed with water and concentrated to dryness in vacuo to give the title compound.

EXAMPLE 97

Preparation of 5-Chloro-3[(4-fluorophenyl)sulfonyl]-7-(4-methylpiperazin-1-yl)-1H-indazole

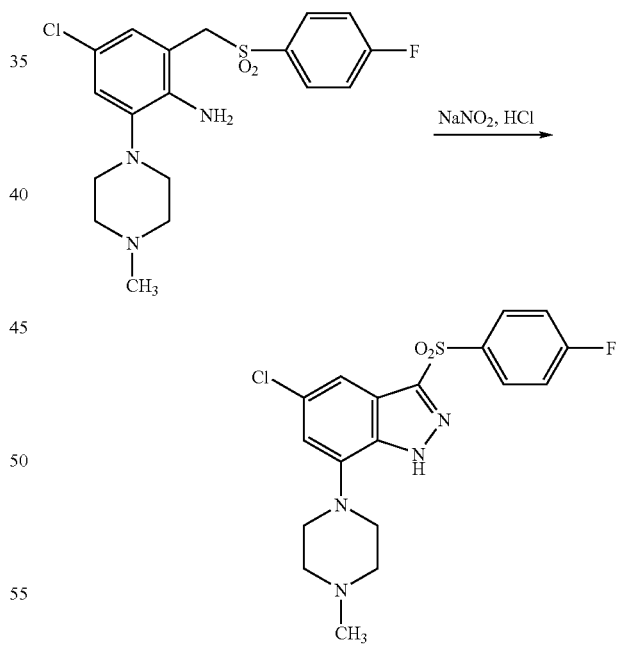

A solution of NaNO₂ (22.0 mg) in water at 0° C. is treated dropwise with a solution of 4-chloro-2-{[(4-fluorophenyl)sulfonyl]methyl}-6-(4-methylpiperazin-1-yl)aniline (102.2 mg, 0.25 mmol) in 1M HCl, allowed to warm to room temperature over a 2 h period, treated with saturated Na₂CO₃ to pH>10 and filtered. The filtercake is washed with water and dried in vacuo to give the title compound, identified by mass spectral and NMR analyses.

EXAMPLE 98–101

Preparation of 3 (Arylsulfonyl)-7-(4-methylpiperazin-1-yl)-1H-indazole Derivatives

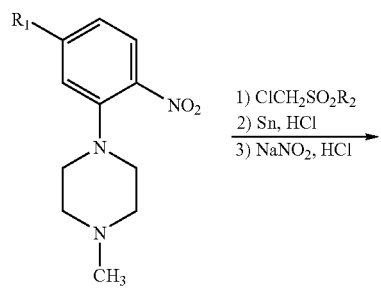

Using essentially the same procedures described hereinabove in Examples 95–97 and employing the appropriate chloromethylarylsulfone, the compounds shown in Table II are obtained and identified by mass spectral and NMR analyses.

TABLE II

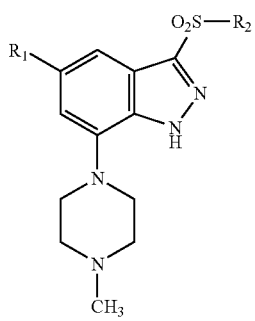

| Ex. No. | R1 | R2 | % Yield (Over 3 Steps) |
|---|---|---|---|
| 98 | Cl | 4-(2-propyl)phenyl | 74 |
| 99 | Cl | 3-(trifluoromethyl)phenyl | 65 |
| 100 | Cl | 1-naphthyl | 7.7 |
| 101 | H | 1-naphthyl | — |

EXAMPLE 102

Preparation of 1-Fluoro-3-[4-(t-butoxycarbonyl)piperazin-1-yl]benzaldehyde

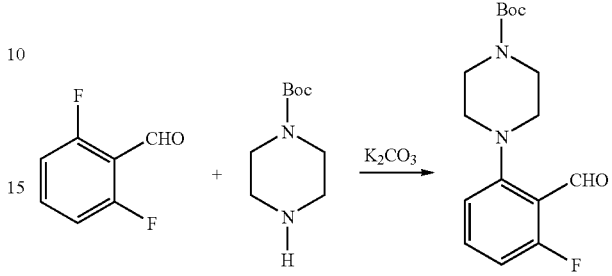

A stirred solution of 2,6-difluorobenzaldehyde 5 (10.0 g, 70 mmol) in N,N-dimethylformamide is treated with tert-butyl piperazine-1-carboxylate (14.4 g, 77.0 mmol) and potassium carbonate (11.7 g, 85.0 mmol), stirred at 80° C. for 16 h, cooled to ambient temperature, diluted with water and extracted with methylene chloride. The extracts are combined, washed sequentially with water and brine, dried over sodium sulfate, and concentrated in vacuo to afford a crude oil. This oil is purified by column chromatography (silica gel, 15:85 ethyl acetate/hexanes) to afford the title compound as a yellow solid, 15.5 g (71% yield), identified by NMR and mass spectral analyses.

EXAMPLE 103

Preparation of 4-[4-(t-Butoxycarbonyl)piperazin-1-yl]-1H-indazole

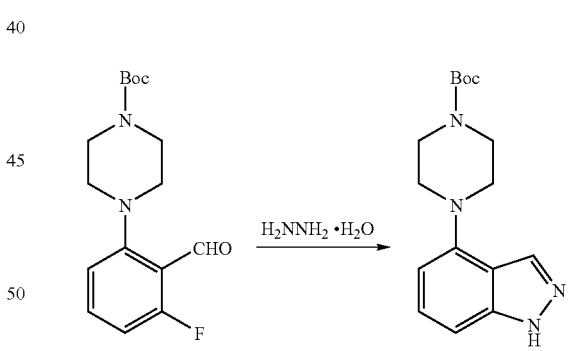

A solution of 1-fluoro-3-[4-(t-butoxycarbonyl)piperazin-1-yl]benzaldehyde (20.0 g, 64.9 mmol) and hydrazine monohydrate (30 mL) in methyl sulfoxide is stirred at 95° C. for 96 h, cooled to room temperature, partitioned between saturated sodium bicarbonate and ether. The phases are separated and the aqueous phase is extracted with ether. The extracts are combined with the organic phase, washed sequentially with water and brine, dried over sodium sulfate and concentrated in vacuo to a crude residue. This residue is purified by column chromatography (silica gel, 10:90 to 30:70 ethyl acetate/hexanes) to afford the title compound as a light yellow solid, 12.3 g (57% yield), identified by NMR and mass spectral analyses.

EXAMPLE 104

Preparation of 4-[4-(t-Butoxycarbonyl)piperazin-1-yl]-3-iodo-1H-indazole

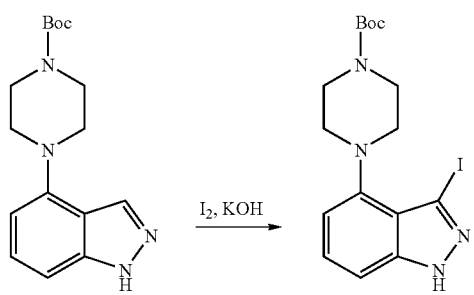

A solution of 4-[4-(t-butoxycarbonyl)piperazin-1-yl]-1H-indazole (5.00 g, 16.5 mmol) in N,N-dimethylformamide is treated with powdered potassium hydroxide (1.85 g, 33.07 mmol) and iodine (4.61 g, 18.2 mmol), stirred at room temperature for 16 h, diluted with ethyl acetate and quenched with 15% aqueous sodium metabisulfite. The phases are separated and the aqueous phase is extracted with ethyl acetate. The extracts and the organic phase are combined, washed with brine, dried over sodium sulfate and concentrated in vacuo to afford a crude solid. This solid is purified by column chromatography (silica gel, 10:90 to 15:85 to 20:80 ethyl acetate/hexanes) to afford the title product as a yellow solid, 2.40 g (35% yield) identified by HNMR and mass spectral analyses.

EXAMPLE 105

Preparation of 4-[4-(t-Butoxycarbonyl)piperazin-1-yl]-3-(phenylsulfonyl)-1H-indazole

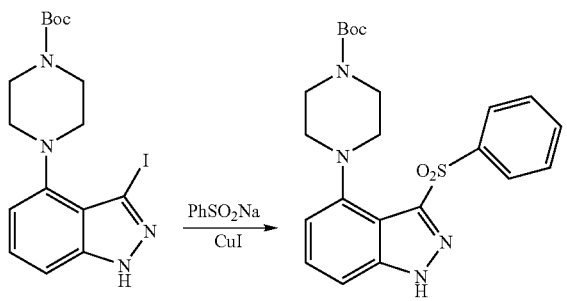

A mixture of 4-[4-(t-butoxycarbonyl)piperazin-1-yl]-3-iodo-1H-indazole (0.110 g, 0.257 mmol), sodium benzene sulfinate (0.068 g, 0.411 mmol), copper(I) iodide (0.073 g, 0.386 mmol) and N,N-dimethylformamide is added to a screw-capped test-tube with Teflon-lined septum. The tube is evacuated and backfilled with argon. This procedure is repeated twice, then the tube is heated to 125° C. for 4 h. The reaction mixture is cooled, partitioned between ethyl acetate and water and filtered through a pad of diatomaceous earth. The filtrate is separated. The organic phase is washed with brine, dried over sodium sulfate and concentrated in vacuo. The resulting crude material is purified by column chromatography (silica gel, 40:60 ethyl acetate/hexanes) to afford the title compound as a pale yellow foam, 0.022 g (18% yield), identified by NMR and mass spectral analyses.

EXAMPLE 106

Preparation of 3-(Phenylsulfonyl)-4-piperazin-1-yl-1H-indazole Hydrochloride

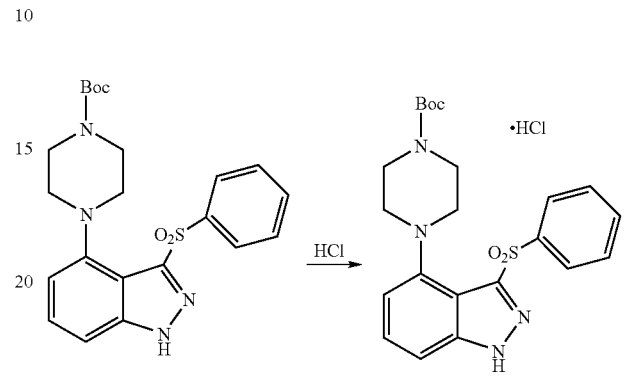

A solution of 4-[4-(t-butoxycarbonyl)piperazin-1-yl]-3-(phenylsulfonyl)-1H-indazole (0.022 g, 0.050 mmol) in methanol is treated with a 2 M solution of HCl in ether (0.4 mL), heated at reflux temperature for 1 h, cooled to room temperature and evaporated to dryness. The residue is re-dissolved in methanol and concentrated. Repeating this procedure three more times affords the title product as a white solid, 0.009 g (40% yield), identified by NMR and mass spectral analyses.

EXAMPLE 107

Preparation of 4-[4-(t-Butoxycarbonyl)piperazin-1-yl]-3-(1-naphthylthio)-1H-indazole

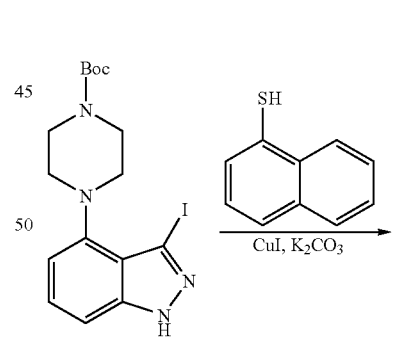

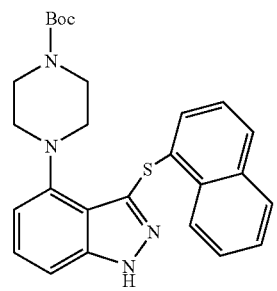

A mixture of 4-[4-(t-butoxycarbonyl)piperazin-1-yl]-3-iodo-1H-indazole (0.068 g, 0.159 mmol), copper(I) iodide (0.005 g, 0.024 mmol) and potassium carbonate (0.044 g, 0.318 mmol) are added to a screw-capped test tube with a Teflon-lined septum. The tube is evacuated and backfilled with argon and this procedure repeated twice more. The reaction mixture is treated sequentially with 2-propanol (1.5 mL), ethylene glycol (19 μL, 0.318 mmol) and 1-naphthalenethiol (0.051 g, 0.318 mmol), heated at 130°–140° C. for 8 h, cooled to room temperature, diluted with ethyl acetate and filtered through diatomaceous earth. The filtrate is concentrated under reduced pressure. The resultant crude material is purified by flash chromatography (silica gel, 40:60 ethyl acetate/hexanes) to afford the title compound as a colorless oil, 0.033 g (45% yield), identified by NMR and mass spectral analyses.

EXAMPLE 108

Preparation of 4-[4-(t-Butoxycarbonyl)piperazin-1-yl]-3-(1-naphthylsulfonyl)-1H-indazole

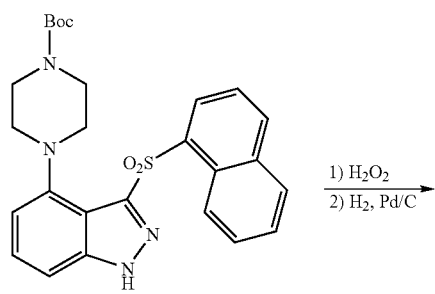

A stirred solution of 4-[4-t-butoxycarbonyl)piperazin-1-yl)-3-(1-naphthylthio)-1H-indazole (0.030 g, 0.065 mmol) in glacial acetic acid is treated with 35% aqueous hydrogen peroxide (0.127 g, 1.30 mmol) stirred for 24 h, quenched with 10% aqueous sodium metabisulfite solution (1 mL) and concentrated in vacuo. The resulting solid is directly added to a suspension of 10% palladium-on-carbon (3 mg) in methanol (10 mL) and the mixture is shaken on a Parr hydrogenator under a 40 psi hydrogen atmosphere for 2 h and filtered through diatomaceous earth. The filtrate is concentrated in vacuo. Purification of the resulting crude material by flash chromatography (silica gel, 30:70 ethyl acetate/hexanes) affords the title compound as a colorless oil, 0.011 g (35% yield), identified by NMR and mass spectral analyses.

EXAMPLE 109

Preparation of 3-(1-Naphthylsulfonyl)-4-piperazin-1-yl-1H-indazole Hydrochloride

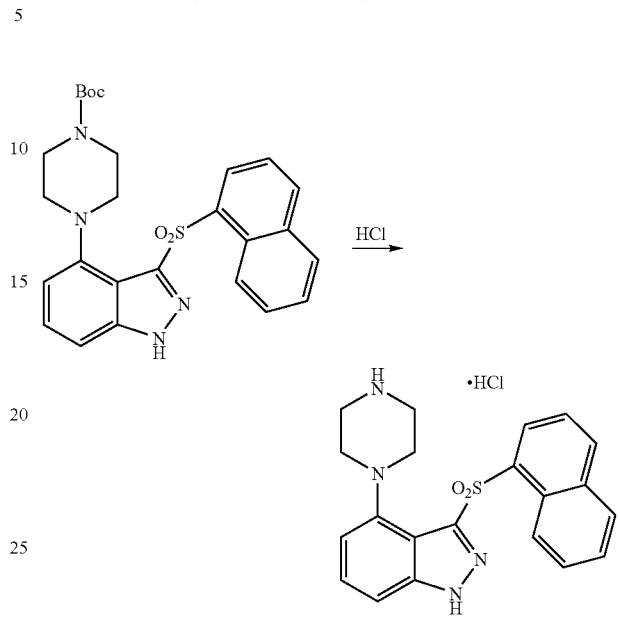

Using essentially the same procedure described in Example 106 hereinabove and employing 4-[4-(t-butoxycarbonyl)piperazin-1-yl]-3-(1-naphthylsulfonyl)-1H-indazole as substrate, the title product is obtained as a light yellow solid (74% yield), mp 220° C. dec, identified by NMR and mass spectral analyses.

EXAMPLES 110–114

Preparation of 3-(Arylsulfonyl)-4-piperazin-1-yl-1H-indazole Hydrochloride Derivatives

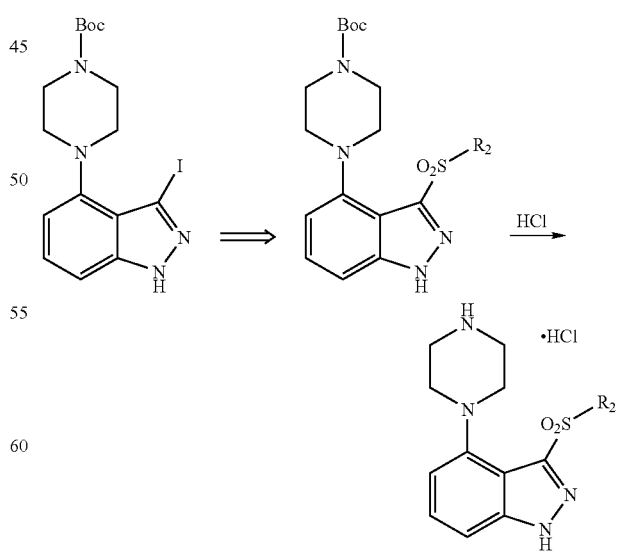

Using essentially the same procedures described in Examples 102–109 hereinabove and employing the appropriate arylthiol or sodium arylsulfinate, the compounds shown on Table III are obtained and identified by NMR and mass spectral analyses.

TABLE III

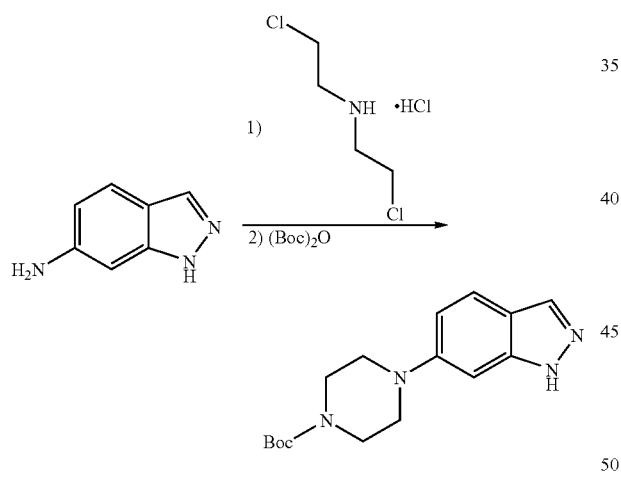

| Ex. No. | R2 | mp ° C. |
|---|---|---|
| 110 | 4-methylphenyl | 190–192 |
| 111 | 4-chlorophenyl | 230 (dec) |
| 112 | 3-fluorophenyl | 180–183 |
| 113 | 4-methoxyphenyl | 178–182 |
| 114 | 2-naphthyl | 200–202 |

EXAMPLE 115

Preparation of 6-[4-t-Butoxycarbonyl)piperazin-1-yl]-1H-indazole

A stirred solution of 6-aminoindazole (13.3 g, 100 mmol) in n-butanol is treated with bis(2-chloroethyl)amine hydrochloride (28.6 g, 160 mmol) and potassium carbonate (34.6 g, 250 mmol), heated at reflux temperature for 72 h, cooled to room temperature and concentrated in vacuo. A stirred solution of the resultant crude material in 1,4-dioxane at 0° C. is treated with 1 N sodium hydroxide solution (200 mL) and di-tert-butyldicarbonate (34.9 g, 160 mmol), stirred at ambient temperature for 24 h and concentrated in vacuo to afford a crude oil. This oil is partitioned between ethyl acetate and water. The organic layer is separated, washed with brine, dried over sodium sulfate and concentrated in vacuo. Further purification of this resultant residue by flash chromatography (silica gel, 40:60 ethyl acetate/hexanes) affords the title compound as a colorless oil, 11.5 g (38% yield) identified by NMR and mass spectral analyses.

EXAMPLE 116

Preparation of 6-[4-(t-Butoxycarbonyl)piperazin-1-yl]-3-iodo-1H-indazole

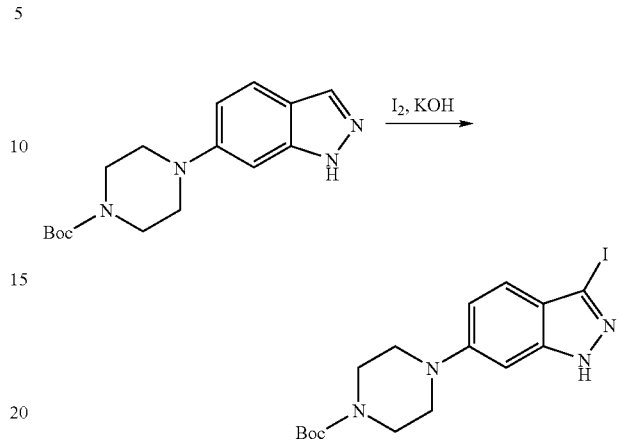

A stirred solution of 6-[4-(t-butoxycarbonyl)piperazin-1-yl]-1H-indazole (7.20 g, 23.8 mmol) in N,N-dimethylformamide at 0° C. is treated with powdered potassium hydroxide (5.40 g, 95.4 mmol) followed by the dropwise addition of a solution of iodine (10.9 g, 42.9 mmol) in N,N-dimethylformamide, stirred at ambient temperatures for 16 h, diluted with ethyl acetate and quenched with 10% aqueous sodium metabisulfite solution. The phases are separated. The aqueous phase is extracted with ethyl acetate. The extracts are combined with the organic phase, washed with brine, dried over sodium sulfate and concentrated in vacuo. The resulting crude material is purified by flash chromatography (silica gel, 30:70 ethyl acetate/hexanes) to afford the title compound as a yellow solid, 3.4 g (38% yield) identified by NMR and mass spectral analyses.

EXAMPLE 117

Preparation of 6-[4(-t-Butoxycarbonyl)piperazin-1-yl]-3-(phenylsulfunoyl)-1H-indazole

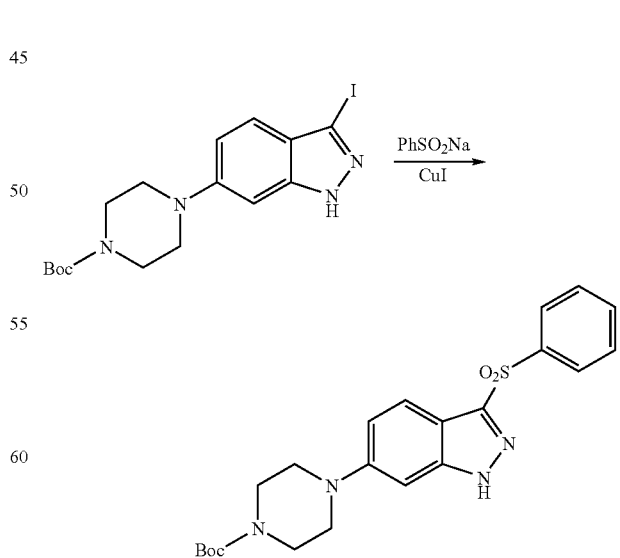

Using essentially the same procedure described in Example 105 hereinabove and employing of 6-[4-(t-butoxycarbonyl)piperazin-1-yl]-3-iodo-1H-indazole and sodium benzenesulfinate affords the title compound as a colorless foam (80% yield), identified by NMR and mass spectral analyses.

EXAMPLE 118

Preparation of 3-(Phenylsulfonyl)-6-piperazin-1-yl-1H-indazole Hydrochloride

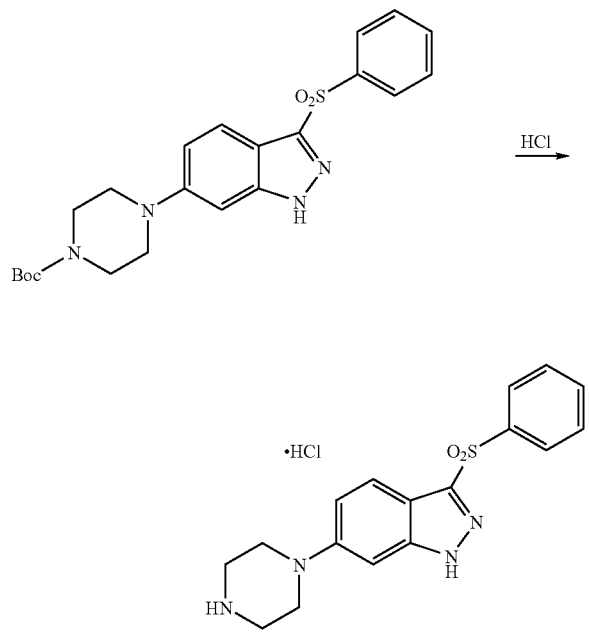

Using essentially the same procedure described in Example 106 hereinabove and employing 6-[4-(t-butoxycarbonyl)piperazin-1-yl]-3-(phenylsulfonyl)-1H-indazole as substrate, the title compound is obtained as an off-white solid (81% yield), identified by NMR and mass spectral analyses.

EXAMPLES 119–124

Preparation of 3-(Arylsulfonyl)-6-piperazin-1-yl-1H-indazole Hydrochloride Compounds

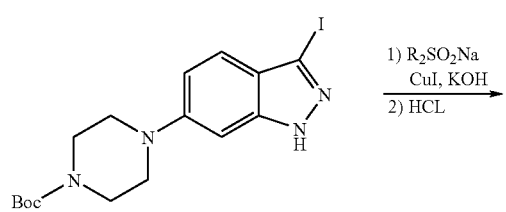

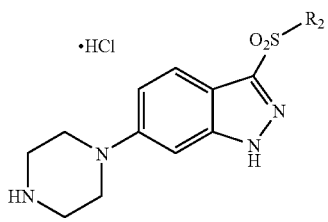

Using essentially the same procedures described in Examples 117 and 118 hereinabove and employing the appropriate sodium arylsulfinate, the compounds shown in Table IV are obtained and identified by NMR and mass spectral analyses.

TABLE IV

| Ex. No. | R2 | mp ° C. |
|---|---|---|
| 119 | 4-methylphenyl | 172–175 |
| 120 | 4-(trifluoromethyl)phenyl | 189–191 |
| 121 | 4-chlorophenyl | 175–178 |
| 122 | 3-fluorophenyl | 260 dec |
| 123 | 4-methoxyphenyl | 165–170 |
| 124 | 2-naphthyl | 260 dec |

EXAMPLE 125

Preparation of 6-[4-(t-Butoxycarbonyl)piperazin-1-yl]-3-(1-naphthylthio)-1H-indazole

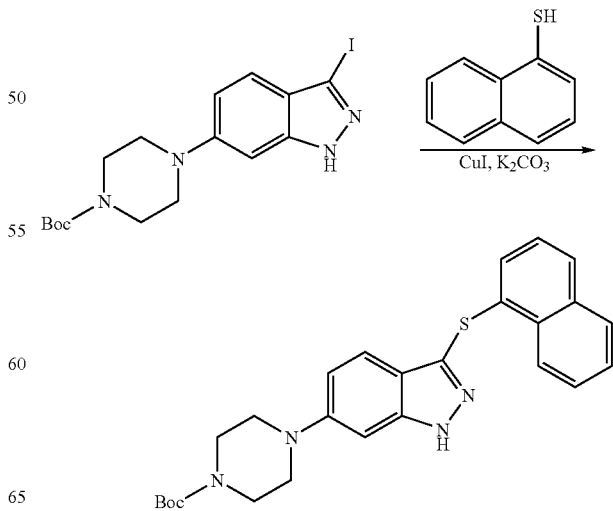

Using essentially the same procedure described in Example 107 hereinabove and employing 6-[4-(t-butoxycarbonyl)piperazin-1-yl]-3-iodo-1H-indazole as substrate, the title compound is obtained as a colorless oil (78% yield), identified by NMR and mass spectral analyses.

EXAMPLE 126

Preparation of 6-[4-t-Butoxycarbonyl)piperazin-1-yl]-3-(1-naphthylsulfonyl)-1H-indazole

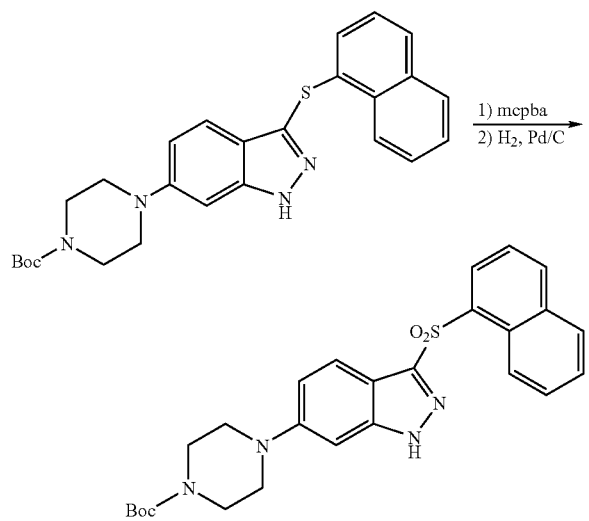

A stirred solution of 6-[4-(t-butoxycarbonyl)piperazin-1-yl]-3-(1-naphthylthio)-1H-indazole (0.240 g, 0.521 mmol) in methylene chloride is treated with meta-chloroperoxybenzoic acid (mcpba) (77% pure, 0.350 g, 1.56 mmol) and sodium bicarbonate (0.219 g, 2.61 mmol), stirred at ambient temperatures for 16 h and partitioned between ethyl acetate and water. The phases are separated and the aqueous phase is extracted with methylene chloride. The extracts and the organic phase are combined, washed sequentially with 10% aqueous sodium bicarbonate solution and brine, dried over sodium sulfate and concentrated in vacuo to afford a crude oil. This oil is added to a suspension of 10% palladium-on-carbon (40 mg) in methanol and shaken on a Parr hydrogenator under a 40 psi hydrogen atmosphere for 2 h and filtered through diatomaceous earth. The filtrate is concentrated in vacuo. The resulting crude material is purified by flash chromatography (silica gel, 50:50 ethyl acetate/hexanes) to afford the title compound as a colorless oil, 0.106 g (41% yield), identified by NMR and mass spectral analyses.

EXAMPLE 127

Preparation of 3-(1-Naphthylsulfonyl)-6-piperazin-1-yl-1H-indazole Hydrochloride

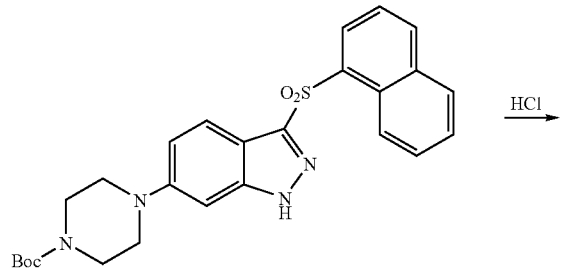

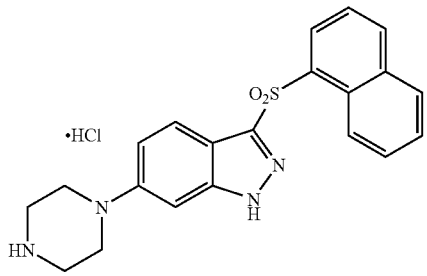

Using essentially the same procedure described in Example 106 hereinablove and employing of 6-[4-(t-butoxycarbonyl)piperazin-1-yl]-3-(1-naphthylsulfonyl)-1H-indazole as substrate, the title product is obtained as a white solid (98% yield), mp 205–210° C., identified by NMR and mass spectral analyses.

EXAMPLE 128

Comparative Evaluation of 5-HT6 Binding Affinity of Test Compounds

The affinity of test compounds for the serotonin 5-HT6 receptor is evaluated in the following manner. Cultured Hela cells expressing human cloned 5-HT6 receptors are harvested and centrifuged at low speed (1,000×g) for 10.0 min to remove the culture media. The harvested cells are suspended in half volume of fresh physiological phosphate buffered saline solution and recentrifuged at the same speed. This operation is repeated. The collected cells are then homogenized in ten volumes of 50 mM Tris.HCl (pH 7.4) and 0.5 mM EDTA. The homogenate is centrifuged at 40,000×g for 30.0 min and the precipitate is collected. The obtained pellet is resuspended in 10 volumes of Tris.HCl buffer and recentrifuged at the same speed. The final pellet is suspended in a small volume of Tris.HCl buffer and the tissue protein content is determined in aliquots of 10–25 μl volumes. Bovine Serum Albumin is used as the standard in the protein determination according to the method described in Lowry et al., *J. Biol. Chem.*, 193:265 (1951). The volume of the suspended cell membranes is adjusted to give a tissue protein concentration of 1.0 mg/ml of suspension. The prepared membrane suspension (10 times concentrated) is aliquoted in 1.0 ml volumes and stored at −70° C. until used in subsequent binding experiments.

Binding experiments are performed in a 96 well microtiter plate format, in a total volume of 200 μl. To each well is added the following mixture: 80.0 μl of incubation buffer made in 50 mM Tris.HCl buffer (pH 7.4) containing 10.0 mM $MgCl_2$ and 0.5 mM EDTA and 20 μl of [$^3$H]-LSD (S.A., 86.0 Ci/mmol, available from Amersham Life Science), 3.0 nM. The dissociation constant, $K_D$ of the [$^3$H]LSD at the human serotonin 5-HT6 receptor is 2.9 nM, as determined by saturation binding with increasing concentrations of [$^3$H]LSD. The reaction is initiated by the final addition of 100.0 μl of tissue suspension. Nonspecific binding is measured in the presence of 10.0 μM methiothepin. The test compounds are added in 20.0 μl volume.

The reaction is allowed to proceed in the dark for 120 min at room temperature, at which time, the bound ligand-receptor complex is filtered off on a 96 well unifilter with a Packard Filtermate® 196 Harvester. The bound complex caught on the filter disk is allowed to air dry and the radioactivity is measured in a Packard TopCount® equipped with six photomultiplier detectors, after the addition of 40.0 µl Microscint®-20 scintillant to each shallow well. The unifilter plate is heat-sealed and counted in a PackardTopCount® with a tritium efficiency of 31.0%.

Specific binding to the 5-HT6 receptor is defined as the total radioactivity bound less the amount bound in the presence of 10.0 µM unlabeled methiothepin. Binding in the presence of varying concentrations of test compound is expressed as a percentage of specific binding in the absence of test compound. The results are plotted as log % bound versus log concentration of test compound. Nonlinear regression analysis of data points with a computer assisted program Prism® yields both the $IC_{50}$ and the $K_i$ values of test compounds with 95% confidence limits.

The amount of displacement by the test compound is given in percent (%) inhibition and is derived from the following equation:

$$\% \text{ inhibition} = \left(1 - \frac{B_0 - NSB}{TB - NSB}\right)100$$

where $B_0$ is the amount of CPM bound in the presence of the testing agent. NSB represents the CPM bound in the presence of a saturating concentration of a displacer and TB represents the total amount of CPM bound at zero (0) concentration of test compound.

Alternatively, a linear regression line of data points is plotted, from which the $IC_{50}$ value is determined and the $K_i$ value is determined based upon the following equation:

$$K_i = IC_{50}/(1 + L/K_D)$$

where L is the concentration of the radioactive ligand used and $K_D$ is the dissociation constant of the ligand for the receptor, both expressed in nM.

Using this assay, the % inhibition and Ki values are determined and compared to those values obtained by representative compounds known to demonstrate binding to the 5-HT6 receptor. The data are shown in Table V, below.

TABLE V

| Ex. No. | 5-HT6 Binding Ki (nM) | % Inhibition at 1 µM |
|---|---|---|
| 4 | 86 | — |
| 5 | — | 53 |
| 7 | 113 | — |
| 8 | 399 | — |
| 9 | 97 | — |
| 10 | 224 | — |
| 11 | — | 67 |
| 12 | 64 | — |
| 13 | 2 | — |
| 14 | 1 | — |
| 15 | 2 | — |
| 16 | 13 | — |
| 17 | 7 | — |
| 18 | 6 | — |
| 19 | 2 | — |
| 20 | — | 63 |
| 21 | — | 22 |
| 22 | — | 25 |
| 23 | — | 5 |
| 24 | — | 23 |
| 25 | — | 74 |
| 26 | — | 8 |
| 27 | — | 13 |
| 28 | 136 | — |
| 29 | — | 24 |
| 30 | — | 30 |
| 31 | 3 | — |
| 32 | 18 | — |
| 33 | 19 | — |
| 34 | 135 | — |
| 35 | 38 | — |
| 36 | 20 | — |
| 37 | 4 | — |
| 38 | 73 | — |
| 39 | 69 | — |
| 40 | 62 | — |
| 41 | 13 | — |
| 42 | 117 | — |
| 43 | 3 | — |
| 44 | — | 67 |
| 45 | 2 | — |
| 46 | 2 | — |
| 47 | 2 | — |
| 48 | 4 | — |
| 49 | 6 | — |
| 50 | 2 | — |
| 51 | 1 | — |
| 52 | 2 | — |
| 53 | 1 | — |
| 54 | 8 | — |
| 55 | 1 | — |
| 56 | 5 | — |
| 58 | 3 | — |
| 59 | 2 | — |
| 60 | 5 | — |
| 63 | 1 | — |
| 64 | 12 | — |
| 65 | 4 | — |
| 66 | 1 | — |
| 67 | 8 | — |
| 68 | 14 | — |
| 69 | 28 | — |
| 70 | 3 | — |
| 71 | 4 | — |
| 72 | 2 | — |
| 74 | 26 | — |
| 77 | 2 | — |
| 80 | 62 | — |
| 81 | 7 | — |
| 83 | 4 | — |
| 85 | 10 | — |
| 86 | 1 | — |
| 89 | 10 | — |
| 91 | 6 | — |
| 92 | 1 | — |
| 97 | 12 | — |
| 98 | 22 | — |
| 99 | 20 | — |
| 100 | 5 | — |
| 101 | 5 | — |

| Comparative Examples | 5-HT6 binding Ki (nM) |
|---|---|
| Clozapine | 6.0 |
| Loxapine | 41.4 |
| Bromocriptine | 23.0 |
| Methiothepin | 8.3 |
| Mianserin | 44.2 |
| Olanzepine | 19.5 |

What is claimed is:
1. A compound of formula I

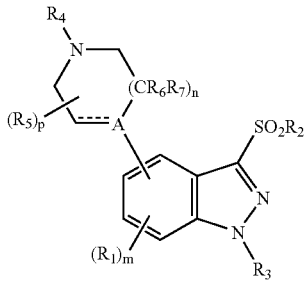

(I)

wherein
A is N;
$R_1$ is H, halogen, CN, $OR_{17}$ or a $C_1$–$C_6$alkyl, or $C_3$–$C_7$cycloalkyl group each optionally substituted;
$R_2$ is an optionally substituted $C_1$–$C_6$alkyl, $C_3$–$C_7$cycloalkyl, aryl, or heteroaryl group
$R_3$ is H or a $C_1$–$C_6$alkyl, or $C_3$–$C_7$cycloalkyl group each optionally substituted;
$R_4$ is H or a $C_1$–$C_6$alkyl or $C_3$–$C_7$cycloalkyl group each optionally substituted;
$R_5$, $R_6$ and $R_7$ are each independently H or a $C_1$–$C_6$alkyl or $C_3$–$C_7$cycloalkyl group each optionally substituted;
m and p are each independently an integer of 1, 2 or 3;
n is an integer of 1;
$R_{17}$ is H or a $C_1$–$C_6$alkyl, $C_2$–$C_6$alkenyl, $C_2$–$C_6$alkynyl, or $C_3$–$C_6$cycloalkyl group each optionally substituted; and
----- represents a single bond; or
the stereoisomers thereof or the pharmaceutically acceptable salts thereof.

2. The compound according to claim 1 wherein $R_4$ is H or an optionally substituted $C_1$–$C_4$alkyl group.

3. The compound according to claim 1 wherein $R_2$ is an optionally substituted phenyl, naphthyl or heteroaryl group.

4. The compound according to claim 1 wherein the 6-membered azacyclic ring is attached to the indazole in the 5 or 7 position.

5. The compound according to claim 4 wherein $R_4$ is H or an optionally substituted $C_1$–$C_4$alkyl group.

6. The compound according to claim 1 wherein $R_2$ is an optionally substituted phenyl, naphthyl or heteroaryl group.

7. The compound according to claim 1 selected from the group consisting of:
5-(4-methylpiperazin-1-yl)-3-(1-naphthylsulfonyl)-1H-indazole;
3-(1-naphthylsulfonyl)-5-piperazin-1-yl-1H-indazole;
3-(1-naphthylsulfonyl)-7-piperazin-1-yl-1H-indazole;
1-(3-chlorobenzyl)-5-(4-methylpiperazin-1-yl)-3-(1-naphthylsulfonyl)-1H-indazole;
7-(4-methylpiperazin-1-yl)-3-(phenylsulfonyl)-1H-indazole;
3-(phenylsulfonyl)-7-(4-propylpiperazin-1-yl)-1H-indazole;
3-(phenylsulfonyl)-7-piperazin-1-yl-1H-indazole;
5-(4-methylpiperazin-1-yl)-3-(phenylsulfonyl)-1H-indazole;
3-(phenylsulfonyl)-5-(4-propylpiperazin-1-yl)-1H-indazole;
3-(phenylsulfonyl)-5-piperazin-1-yl-1H-indazole;
5-piperazin-1-yl-3-[(3-cyanophenyl)sulfonyl]-1H-indazole;
7-(4-methylpiperazin-1-yl)-3-[(2-phenethyl)sulfonyl]-1H-indazole;
3-(1-naphthylsulfonyl)-7-(4-propylpiperazin-1-yl)-1H-indazole;
5-(4-phenethylpiperazin-1-yl)-3-(1-naphthylsulfonyl)-1H-indazole;
5-(4-methylpiperazin-1-yl)-3-(2-naphthylsulfonyl)-1H-indazole;
3-[(2-chloro-4-fluorophenyl)sulfonyl]-5-piperazin-1-yl-1H-indazole;
1-methyl-3-(phenylsulfonyl)-5-piperazin-1-yl-1H-indazole;
1-phenyl-3-(phenylsulfonyl)-5-piperazin-1-yl-1H-indazole;
1-methyl-3-(phenylsulfonyl)-7-piperazin-1-yl-1H-indazole;
1-phenyl-3-(phenylsulfonyl)-7-piperazin-1-yl-1H-indazole;
7-piperazin-1-yl-3-[(3-fluorophenyl)sulfonyl]-1H-indazole;
3-[(4-fluorophenyl)sulfonyl]-7-(4-methylpiperazin-1-yl)-1H-indazole;
3-[(2-chlorophenyl)sulfonyl]-7-piperazin-1-yl-1H-indazole;
3-[(4-aminophenyl)sulfonyl]-7-piperazin-1-yl-1H-indazole;
5-piperazin-1-yl-3-[(3-fluorophenyl)sulfonyl]-1H-indazole;
3-[(4-fluorophenyl)sulfonyl]-5-(4-methylpiperazin-1-yl)-1H-indazole;
3-[(2-chlorophenyl)sulfonyl]-5-(4-propylpiperazin-1-yl)-1H-indazole;
3-[(4-aminophenyl)sulfonyl]-5-piperazin-1-yl-1H-indazole;
3-[(5-chlorothien-2-yl)sulfonyl]-5-piperazin-1-yl-1H-indazole;
3-[(5-chlorothien-2-yl)sulfonyl]-7-piperazin-1-yl-1H-indazole;
4-chloro-3-(phenylsulfonyl)-7-piperazin-1-yl-1H-indazole;
5-fluoro-3-(phenylsulfonyl)-7-piperazin-1-yl-1H-indazole;
6-fluoro-3-(phenylsulfonyl)-7-piperazin-1-yl-1H-indazole;
4-chloro-3-(phenylsulfonyl)-5-piperazin-1-yl-1H-indazole;
7-fluoro-3-(phenylsulfonyl)-5-piperazin-1-yl-1H-indazole;
6-fluoro-3-(phenylsulfonyl)-5-piperazin-1-yl-1H-indazole;
6-(4-phenethylpiperazin-1-yl)-3-(phenylsulfonyl)-1H-indazole;
6-(4-methylpiperazin-1-yl)-3-(phenylsulfonyl)-1H-indazole;
6-(4-propylpiperazin-1-yl)-3-(phenylsulfonyl)-1H-indazole;
3-(phenylsulfonyl)-6-piperazin-1-yl-1H-indazole;
4-piperazin-1-yl-3-(phenylsulfonyl)-1H-indazole;
4-(4-methylpiperazin-1-yl)-3-(phenylsulfonyl)-1H-indazole;
4-(4-propylpiperazin-1-yl)-3-(phenylsulfonyl)-1H-indazole;
3-(phenylsulfonyl)-4-piperazin-1-yl-1H-indazole;
the stereoisomers thereof; and
the pharmaceutically acceptable salts thereof.

8. A pharmaceutical composition which comprises at least one pharmaceutically acceptable carrier and an effective amount of compound of formula I

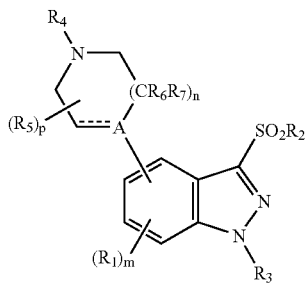

wherein
A is N;
R$_1$ is H, halogen, CN, OR$_{17}$ or a C$_1$–C$_6$alkyl, or C$_3$–C$_7$cycloalkyl group each optionally substituted;
R$_2$ is an optionally substituted C$_1$–C$_6$alkyl, C$_3$–C$_7$cycloalkyl, aryl, or heteroaryl group
R$_3$ is H or a C$_1$–C$_6$alkyl, or C$_3$–C$_7$cycloalkyl group each optionally substituted;
R$_4$ is H or a C$_1$–C$_6$alkyl or C$_3$–C$_7$cycloalkyl group each optionally substituted;
R$_5$, R$_6$ and R$_7$ are each independently H or a C$_1$–C$_6$alkyl or C$_3$–C$_7$cycloalkyl group each optionally substituted;
m and p are each independently an integer of 1, 2 or 3;
n is an integer of 1;
R$_{17}$ is H or a C$_1$–C$_6$alkyl, C$_2$–C$_6$alkenyl, C$_2$–C$_6$alkynyl, or C$_3$–C$_6$cycloalkyl group each optionally substituted; and
- - - - represents a single bond; or
the stereoisomers thereof or the pharmaceutically acceptable salts thereof.

9. The composition according to claim 8 having a formula I compound wherein R$_4$ is H or an optionally substituted C$_1$–C$_4$alkyl group.

10. The composition according to claim 9 having a formula I compound wherein R$_2$ is an optionally substituted phenyl, naphthyl or heteroaryl group.

11. The composition according to claim 10 having a formula I compound wherein the 6-membered azacyclic ring is attached to the indazole in the 5 or 7 position.

12. The composition according to claim 8 having a formula I compound selected from the group consisting of:
5-(4-methylpiperazin-1-yl)-3-(1-naphthylsulfonyl)-1H-indazole;
3-(1-naphthylsulfonyl)-5-piperazin-1-yl-1H-indazole;
3-(1-naphthylsulfonyl)-7-piperazin-1-yl-1H-indazole;
1-(3-chlorobenzyl)-5-(4-methylpiperazin-1-yl)-3-(1-naphthylsulfonyl)-1H-indazole;
7-(4-methylpiperazin-1-yl)-3-(phenylsulfonyl)-1H-indazole;
3-(phenylsulfonyl)-7-(4-propylpiperazin-1-yl)-1H-indazole;
3-(phenylsulfonyl)-7-piperazin-1-yl-1H-indazole;
5-(4-methylpiperazin-1-yl)-3-(phenylsulfonyl)-1H-indazole;
3-(phenylsulfonyl)-5-(4-propylpiperazin-1-yl)-1H-indazole;
3-(phenylsulfonyl)-5-piperazin-1-yl-1H-indazole;
5-piperazin-1-yl-3-[(3-cyanophenyl)sulfonyl]-1H-indazole;
7-(4-methylpiperazin-1-yl)-3-[(2-phenethyl)sulfonyl]-1H-indazole;
3-(1-naphthylsulfonyl)-7-(4-propylpiperazin-1-yl)-1H-indazole;
5-(4-phenethylpiperazin-1-yl)-3-(1-naphthylsulfonyl)-1H-indazole;
5-(4-methylpiperazin-1-yl)-3-(2-naphthylsulfonyl)-1H-indazole;
3-[(2-chloro-4-fluorophenyl)sulfonyl]-5-piperazin-1-yl-1H-indazole;
1-methyl-3-(phenylsulfonyl)-5-piperazin-1-yl-1H-indazole;
1-phenyl-3-(phenylsulfonyl)-5-piperazin-1-yl-1H-indazole;
1-methyl-3-(phenylsulfonyl)-7-piperazin-1-yl-1H-indazole;
1-phenyl-3-(phenylsulfonyl)-7-piperazin-1-yl-1H-indazole;
7-piperazin-1-yl-3-[(3-fluorophenyl)sulfonyl]-1H-indazole;
3-[(4-fluorophenyl)sulfonyl]-7-(4-methylpiperazin-1-yl)-1H-indazole;
3-[(2-chlorophenyl)sulfonyl]-7-piperazin-1-yl-1H-indazole;
3-[(4-aminophenyl)sulfonyl]-7-piperazin-1-yl-1H-indazole;
5-piperazin-1-yl-3-[(3-fluorophenyl)sulfonyl]-1H-indazole;
3-[(4-fluorophenyl)sulfonyl]-5-(4-methylpiperazin-1-yl)-1H-indazole;
3-[(2-chlorophenyl)sulfonyl]-5-(4-propylpiperazin-1-yl)-1H-indazole;
3-[(4-aminophenyl)sulfonyl]-5-piperazin-1-yl-1H-indazole;
3-[(5-chlorothien-2-yl)sulfonyl]-5-piperazin-1-yl-1H-indazole;
3-[(5-chlorothien-2-yl)sulfonyl]-7-piperazin-1-yl-1H-indazole;
4-chloro-3-(phenylsulfonyl)-7-piperazin-1-yl-1H-indazole;
5-fluoro-3-(phenylsulfonyl)-7-piperazin-1-yl-1H-indazole;
6-fluoro-3-(phenylsulfonyl)-7-piperazin-1-yl-1H-indazole;
4-chloro-3-(phenylsulfonyl)-5-piperazin-1-yl-1H-indazole;
7-fluoro-3-(phenylsulfonyl)-5-piperazin-1-yl-1H-indazole;
6-fluoro-3-(phenylsulfonyl)-5-piperazin-1-yl-1H-indazole;
6-(4-phenethylpiperazin-1-yl)-3-(phenylsulfonyl)-1H-indazole;
6-(4-methylpiperazin-1-yl)-3-(phenylsulfonyl)-1H-indazole;
6-(4-propylpiperazin-1-yl)-3-(phenylsulfonyl)-1H-indazole;
3-(phenylsulfonyl)-6-piperazin-1-yl-1H-indazole;
4-piperazin-1-yl-3-(phenylsulfonyl)-1H-indazole;
4-(4-methylpiperazin-1-yl)-3-(phenylsulfonyl)-1H-indazole;
4-(4-propylpiperazin-1-yl)-3-(phenylsulfonyl)-1H-indazole;
3-(phenylsulfonyl)-4-piperazin-1-yl-1H-indazole;
the stereoisomers thereof; and
the pharmaceutically acceptable salts thereof.

13. 3-(1-naphthylsulfonyl)-5-piperazinyl-1H-indazole or a pharmaceutically acceptable salt thereof.

14. A pharmaceutical composition which comprises at least one pharmaceutically acceptable carrier and an effective amount of 3-(1-naphthylsulfonyl)-5-piperazinyl-1H-indazole or a pharmaceutically acceptable salt thereof.

* * * * *